US010688694B2

(12) United States Patent
Acevedo et al.

(10) Patent No.: US 10,688,694 B2
(45) Date of Patent: Jun. 23, 2020

(54) AUTOMATED FABRICATION OF LAYER-BY-LAYER TISSUE ENGINEERED COMPLEX TUBES

(71) Applicants: UNIVERSIDAD DE LOS ANDES, Santiago (CL); CELLS FOR CELLS S.A., Santiago (CL); Juan Pablo Acevedo, Santiago (CL); Camila Wilkens, Santiago (CL); Maroun Khoury, Santiago (CL); Christopher Rivet, Santiago (CL)

(72) Inventors: Juan Pablo Acevedo, Santiago (CL); Camila Wilkens, Santiago (CL); Maroun Khoury, Santiago (CL); Christopher Rivet, Santiago (CL)

(73) Assignees: UNIVERSIDAD DE LOS ANDES, Santiago (CL); CELLS FOR CELLS S.A., Santiago (CL); Juan Pablo Acevedo, Santiago (CL); Camila Wilkens, Santiago (CL); Maroun Khoury, Santiago (CL); Christopher Rivet, Santiago (CL)

(*) Notice: Subject to any disclaimer, the term of this patent is extended or adjusted under 35 U.S.C. 154(b) by 54 days.

(21) Appl. No.: 15/768,161

(22) PCT Filed: Oct. 14, 2016

(86) PCT No.: PCT/IB2016/056176
§ 371 (c)(1),
(2) Date: Apr. 13, 2018

(87) PCT Pub. No.: WO2017/064667
PCT Pub. Date: Apr. 20, 2017

(65) Prior Publication Data
US 2018/0304502 A1    Oct. 25, 2018

Related U.S. Application Data

(60) Provisional application No. 62/241,558, filed on Oct. 14, 2015.

(30) Foreign Application Priority Data

Jun. 28, 2016   (EP) .................................... 16176767

(51) Int. Cl.
B29C 41/22        (2006.01)
B29C 41/14        (2006.01)
(Continued)

(52) U.S. Cl.
CPC ................ *B29C 41/22* (2013.01); *A61F 2/04* (2013.01); *A61F 2/06* (2013.01); *A61L 27/18* (2013.01);
(Continued)

(58) Field of Classification Search
CPC . B29C 41/22; B29C 41/14; A61F 2/04; A61F 2/06
See application file for complete search history.

(56) References Cited

U.S. PATENT DOCUMENTS

2012/0232643 A1    9/2012 Ramzipoor et al.

OTHER PUBLICATIONS

Barros et al., "Bioresorbable ureteral stents from natural origin polymers," *J. Biomed. Mater. Res. B* 103(3):608-617, 2014.
(Continued)

*Primary Examiner* — Jason-Dennis N Stewart
(74) *Attorney, Agent, or Firm* — Seed IP Law Group LLP

(57) ABSTRACT

The present invention overcomes all the above drawbacks and provides a versatile method for the fabrication of multilayer hollow tubes that uses a layer-by-layer rod dipping approach using different biomaterials. The device enables fine control over fabrication parameters, such as
(Continued)

ascending/descending speeds, rod rotational velocity, and crosslinking or polymerization time. All these technologies allows the generation of more complex multilayer hollow tubes such as vessel-like structures, urethral grafting, prostate grafting and the like.

23 Claims, 15 Drawing Sheets

(51) Int. Cl.
| | |
|---|---|
| A61L 27/34 | (2006.01) |
| A61L 27/50 | (2006.01) |
| A61L 27/38 | (2006.01) |
| A61F 2/04 | (2013.01) |
| A61F 2/06 | (2013.01) |
| A61L 27/18 | (2006.01) |
| A61L 27/20 | (2006.01) |
| A61L 27/22 | (2006.01) |
| A61L 27/26 | (2006.01) |
| A61L 27/36 | (2006.01) |
| A61L 27/54 | (2006.01) |
| A61L 27/58 | (2006.01) |
| B32B 1/08 | (2006.01) |
| B32B 9/02 | (2006.01) |
| B29L 31/00 | (2006.01) |

(52) U.S. Cl.
CPC .............. *A61L 27/20* (2013.01); *A61L 27/222* (2013.01); *A61L 27/26* (2013.01); *A61L 27/34* (2013.01); *A61L 27/3679* (2013.01); *A61L 27/3808* (2013.01); *A61L 27/3813* (2013.01); *A61L 27/3817* (2013.01); *A61L 27/3826* (2013.01); *A61L 27/3834* (2013.01); *A61L 27/3882* (2013.01); *A61L 27/507* (2013.01); *A61L 27/54* (2013.01); *A61L 27/58* (2013.01); *B29C 41/14* (2013.01); *B32B 1/08* (2013.01); *B32B 9/02* (2013.01); *A61F 2002/047* (2013.01); *A61F 2210/0076* (2013.01); *A61F 2240/001* (2013.01); *A61L 2300/604* (2013.01); *A61L 2300/608* (2013.01); *A61L 2300/64* (2013.01); *A61L 2420/02* (2013.01); *A61L 2420/08* (2013.01); *A61L 2430/22* (2013.01); *A61L 2430/32* (2013.01); *B29K 2089/00* (2013.01); *B29L 2031/7534* (2013.01); *B32B 2535/00* (2013.01)

(56) References Cited

OTHER PUBLICATIONS

Lovett et al., "Silk fibroin microtubes for blood vessel engineering," *Biomaterials* 28(35):5271-5279, 2007. (19 pages).

Silva et al., "Nanostructured Hollow Tubes Based on Chitosan and Alginate Multilayers," *Adv. Healthcare Mater.* 3(3):433-440, 2013.

Yue et al., "Synthesis, properties, and biomedical applications of gelatin methacryloyl (GelMA) hydrogels," *Biomaterials* 73:254-271, 2015.

Fig. 19

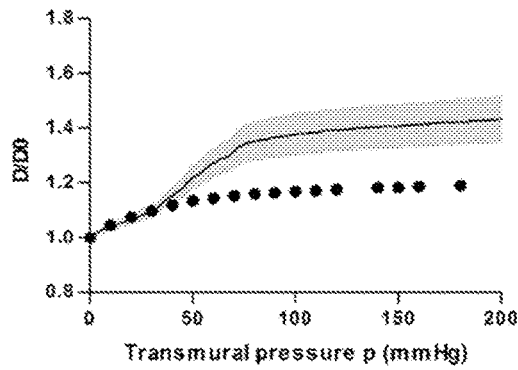

Table 1 | Vascular graft and human coronary artery compliance (%C) ($10^{-2}$ mmHg) at different pressures ranges and $e_z=10\%$

| Pressure range (mmHg) | 50-90 | 80-120 | 110-150 |
|---|---|---|---|
| Vascular graft | 29.2 ± 8.35 | 5.0 ± 2.10 | 4.0 ± 1.39 |
| Coronary artery | 6.3 ± 1.27 | 3.5 ± 0.04 | 2.5 ± 0.43 |

*Statistical difference (p<0.05) compared with vascular graft
**Statistical difference (p<0.005) compared with vascular graft

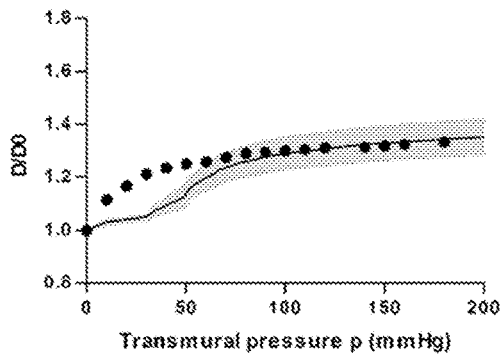

Table 2 | Vascular graft and human coronary artery compliance (%C) ($10^{-2}$ mmHg) at different pressures ranges and $e_z=20\%$

| Pressure range (mmHg) | 50-90 | 80-120 | 110-150 |
|---|---|---|---|
| Vascular graft | 30.2 ± 7.79 | 9.3 ± 1.15 | 5.8 ± 0.43 |
| Coronary artery | 7.3 ± 2.16 | 3.6 ± 2.69 | 2.5 ± 2.10 |

*Statistical difference (p<0.05) compared with vascular graft
**Statistical difference (p<0.005) compared with vascular graft

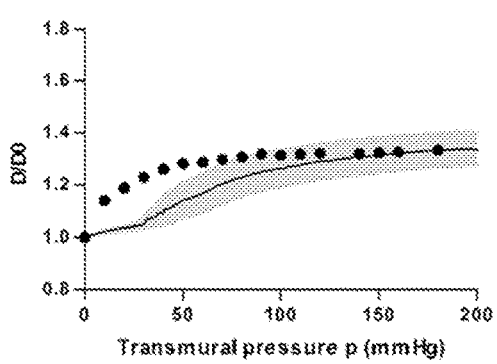

Table 3 | Vascular graft and human coronary artery compliance (%C) ($10^{-2}$ mmHg) at different pressures ranges and $e_z=25\%$

| Pressure range (mmHg) | 50-90 | 80-120 | 110-150 |
|---|---|---|---|
| Vascular graft | 24.0 ± 4.84 | 12.9 ± 2.60 | 7.5 ± 0.98 |
| Coronary artery | 7.1 ± 0.17* | 2.7 ± 0.37* | 1.2 ± 0.65** |

*Statistical difference (p<0.05) compared with vascular graft
**Statistical difference (p<0.005) compared with vascular graft

AUTOMATED FABRICATION OF LAYER-BY-LAYER TISSUE ENGINEERED COMPLEX TUBES

TECHNICAL FIELD

The present invention relates to multilayer hollow tubes and method of productions thereof. The multilayer hollow tubes of the present invention can be produced easily and rapidly and, moreover, present structural configurations that would mimic the one observed in the natural body. Therefore, they can be used in various biomedical applications.

BACKGROUND

In 2012 over 15 million people in the United States were diagnosed with coronary heart disease and it is currently the leading cause of death. Coronary arteries are small diameter blood vessels (SDBV), on average 4 mm in diameter, and once occluded, they pose a serious risk for myocardial infarction. A stent is typically deployed to open-up the narrowed vessel; however, restenosis may occur, necessitating replacement of the vessel. Whereas large diameter blood vessels are readily substituted with Teflon or other synthetic-based constructs, they fall short of meeting the physiological requirements for SDBV, and are only replaced with an autologous graft. Large diameter vessels benefit from high blood flow velocities, which reduce blood-graft interface contact activation, and thereby minimize the potential for thrombus formation. The opposite is true with SDBV; low blood flow velocities increase interface time and the propensity for thrombus formation, which occludes the lumen of vessel grafts. The current standard of care for SDBV bypass surgeries are the internal mammary artery, saphenous vein, radial artery and the right gastroepiploic artery. Nevertheless, this alternative increases the risk of comorbidity and the patients can go through several rounds of surgical procedures. These autografts, although mechanically inferior, provide a blood-compatible vessel solution. However, limited availability and donor site comorbidity are major points of concern for employing an autograft for SDBV. On the other hand, differences in diameter and compliance to the natural vessels in the anastomosis area might lead to intimal hyperplasia and failure of the graft.

Tissue engineered SDBV are poised to replace autografts by recapitulating the native structure and function of blood vessels without requiring tissue to be harvested. Structurally, blood vessels are composed of three distinct layers: the tunica externa (adventitia), tunica media, and tunica intima. The tunica externa primarily provides a protective coating to the vessel, which doubles as an attachment point to tissues. The tunica media consists mainly of smooth muscle cells and elastic tissue, oriented circumferentially around the vessel, providing compliance and resilience to arterial pressure. Finally, the endothelial lining of the tunica intima provides the blood-compatible, luminal interface. Tissue engineering approaches to construct SDBVs have focused their research on recreating the media and the intima layers, because a non-thrombus forming surface and a mechanical behavior and durability are desirable characteristics in engineered grafts.

Many attempts for engineering SDBV consisted of variable scaffold compositions and fabrication techniques intended to replicate vessels' natural layers. Decellularized scaffolds employ the natural structure of allografts to provide the proper extracellular environment for subsequent cell seeding and repopulation. Electrospinning is a novel technique that has been widely reported due to the fibrous, durable matrix it can produce, which can be deposited in an aligned manner, wrapped around the vessel for recreating the mechanical strength that the tunica media has or as a scaffold for cell seeding. A third approach consists in dipping a thin rod into a hydrogel solution, which upon gelation provides a tubular structure. This is a very promising method as it allows an easy layer-by-layer fabrication, recapitulating the unique structure and function of each vascular layer. However, it has neither been explored to generate more complex multilayer vessel-like structures nor used to fabricate cell-laden concentric layers.

Scalability and reproducibility of results is a major concern in the biomedical field, where reports indicate that up to 90% of studies couldn't be reproduced. A reason for the lack of reproducibility is the artist-like, nuanced method by which many studies are performed, especially those of tissue engineering, where each implant is a one-off device. A means for overcoming the just-right methodology is to automate processes using simple robotics, removing the human element and standardizing the process. Never before has this prospect been as available as it is now, with simple, inexpensive microprocessors widely available, such as the Arduino platform. This open-source microprocessor is easy to program and supports a number of "shields" which add functionality to the system, such as a stepper motor driver. By automatizing the fabrication of tissue engineered SDBV it is possible to dramatically increase the production volume and decrease sample-to-sample variability, which can confound results and reduce the project's success and medical translation.

BRIEF DESCRIPTION OF THE INVENTION

The present invention overcomes all the above drawbacks and provides a versatile method for the fabrication of multilayer hollow tubes that uses a layer-by-layer rod dipping approach using different biomaterials. The device enables fine control over fabrication parameters, such as ascending/descending speeds, rod rotational velocity, and crosslinking or polymerization time. All these technologies allows the generation of more complex multilayer hollow tubes such as vessel-like structures, urethral grafting, prostate grafting and the like.

The present invention also describes a paradigm-shifting alternative to cell seeding using a cell-compatible hydrogel that allows cells to be directly incorporated into a matrix instead of post hoc seeding. This method can be carried out by means of an automatized system so that variability is reduced and the significance of the results is increased.

The method of the present invention can be carried out by means of an automatized system thus being versatile, scalable and suitable to easily and rapidly fabricate complex cellularized and non-cellularized multilayer hollow tubes, such as vascular graft etc., with structural configuration that would mimic the one observed in natural blood vessels or special-multi-layer configuration of tubes meant to be used for different biomedical applications.

The method and the automatized system are capable to fine control in a scalable manner the material composition, geometry, spatial location of specialized biomaterials and cells types, among other factors. Thus, the method according to the present invention shows excellent control of biological and mechanical properties, a great control of multilayer thickness, micro-deposition, cell viability and spatial control of components such as biomaterials and cells in the fabrication of multilayer hollow tubes and blood vessel-like structures. The mechanical strength of the materials and the tight interactions between layer interfaces allows the maintenance of the structure, geometry and integrity of the finished tube or vessel.

The automatized methodology according to the present invention enables the fabrication of engineered tubes and blood vessels that uses a layer-by-layer rod dipping approach, and fabrication variables such as dipping speed and viscosity. The method and devices can be adapted to use different biomaterial having different mechanism for polymerization or crosslinking, and capable to homogenously distribute viable cell content, proteins, drugs and polymeric particles, etc., with well-defined patterns across the multilayer vessel grafts.

The multilayer hollow tubes and the method of production thereof can be briefly described below.

(1) A method to produce a multilayer hollow tube comprising the following steps:
  i) dipping a rod into a pre-polymerized solution comprising:
    gelatin; and
    a photo-initiator;
  wherein the gelatin is chemically functionalized to become reactive to polymerization or crosslinking in presence of free radicals;
  ii) exposing the pre-polymerized solution attached to the rod to light, visible, UV light or infrared depending on the nature of the photo-initiator while the rod is rotating and emerging from the pre-polymerized solution to obtain a polymerized or crosslinked layer; and
  iii) repeating steps i) and ii) to obtain the desired number of layers;
  wherein the pre-polymerized solutions used for each layer can have the same or different compositions.

(2) The method according to (1) wherein the amount of functionalized gelatin in the pre-polymerized solution is 1-20% w/v.

(3) The method according to any one of (1) to (2), wherein the gelatin of the pre-polymerized solution in step i) is functionalized with at least a chemical agent selected from the group consisting of methacryloyl groups and acryloyl groups.

(4) The method according to any one of (1) to (3), wherein the pre-polymerized solution comprises 8-12% w/v of methacrylated gelatin and 0.1 to 1% w/v of a photo-initiator.

(5) The method according to any one of (1) to (3), wherein the pre-polymerized solution comprises 10% w/v of methacrylated gelatin and 0.5% w/v of photo-initiator.

(6) The method according to any one of (1) to (5), wherein the pre-polymerized solution further comprises alginate or salts thereof or derivatives thereof.

(7) The method according to any one of (1) to (6), wherein the pre-polymerized solution further comprises 0.15 to 1.5% w/v of alginate or salts thereof or derivatives thereof.

(8) The method according to any one of (1) to (6), wherein the pre-polymerized solution further comprises from 0.075 to 0.15% w/v of alginate or salts thereof or derivatives thereof.

(9) The method according to any one of (1) to (4) and (6) to (7), wherein the pre-polymerized solution comprises 10% w/v of methacrylated gelatin, 0.5% w/v of sodium alginate and 0.2% w/v of photo-initiator.

(10) The method according to any one of (1) to (9), wherein the pre-polymerized solution further comprises at least one compound selected from the group consisting of gelatin chitosan, gellam gum, collagen, elastin, cellulose mixtures thereof, salts thereof and derivatives thereof.

(11) The method according to any one of (1) to (10), wherein the pre-polymerized solution further comprises at least one selected from viable cells, proteins, drugs and polymeric particles.

(12) The method according to any one of (1) to (11), wherein at least one of the layers is coated with polycaprolactone fibres.

(13) The method according to (12) wherein the coating with polycaprolactone fibres is performed by means of solution blow spinning using a solution comprising 1 to 20% w/v of polycaprolactone.

(14) The method according to any one of (12) to (13) wherein the coating with polycaprolactone fibres is performed by means of solution blow spinning using a solution comprising 4% w/v of polycaprolactone.

(15) The method according to any one of (1) to (14), wherein the pre-polymerized solution also comprises cells.

(16) The method according to any one of (1) to (15), wherein the pre-polymerized solution also comprises mature or differentiated cells and/or mesenchymal stem cells.

(17) The method according to any one of (1) to (16) wherein the pre-polymerized solutions used for each layer have different compositions from one another.

(18) The method according to any one of (1) to (17), wherein before step i):
  the rod is dipped at least once in a solution comprising alginate or salts thereof or derivatives thereof; and
  then dipped in a solution inducing polymerization or crosslinking of the alginate or salts thereof or derivatives thereof.

(19) A multilayer hollow tube having a lumen diameter of at least 1.5 mm;
wherein
each layer has a thickness of 1 to 400 μm and comprises polymerized or cross-linked chemically functionalized gelatin and wherein the layers can have the same or different composition from one another.

(20) The multilayer hollow tube of (19) wherein each layer can further comprise gelatin, alginate, chitosan, gellam gum, collagen, elastin, cellulose mixtures thereof, salts thereof and derivatives thereof.

(21) The multilayer hollow tube according to any one of (19) to (20) wherein at least one of the layers comprises at least one selected from viable cell, proteins, drugs and polymeric particles.

(22) The multilayer hollow tube according to any one of (19) to (21) wherein the first layer comprises cells.

(23) The multilayer hollow tube according to any one of (21) to (22) wherein the cells are selected from mature or differentiated cells and/or mesenchymal stem cells.

(24) The multilayer hollow tube according to any one of (19) to (23) wherein at least one of the layers is coated with polycaprolactone fibres.

(25) The multilayer hollow tube according to any one of (19) to (24) which is a blood-like vessel structure or a urethral grafting or a prostate grafting.

BRIEF DESCRIPTION OF THE DRAWINGS

FIG. 19. D/DO vs pressure curves for GelBMa reinforced with PCL fibers vascular graft (line) compared with human coronary arteries (solid circle) (Claes, 2010; van Andel, 2003) at three different values of axial prestretch. a) ez=10% of axial prestretch. b) ez=20% of axial prestretch. c) ez=25% of axial prestretch.

DETAILED DESCRIPTION OF THE INVENTION

Figure 1:
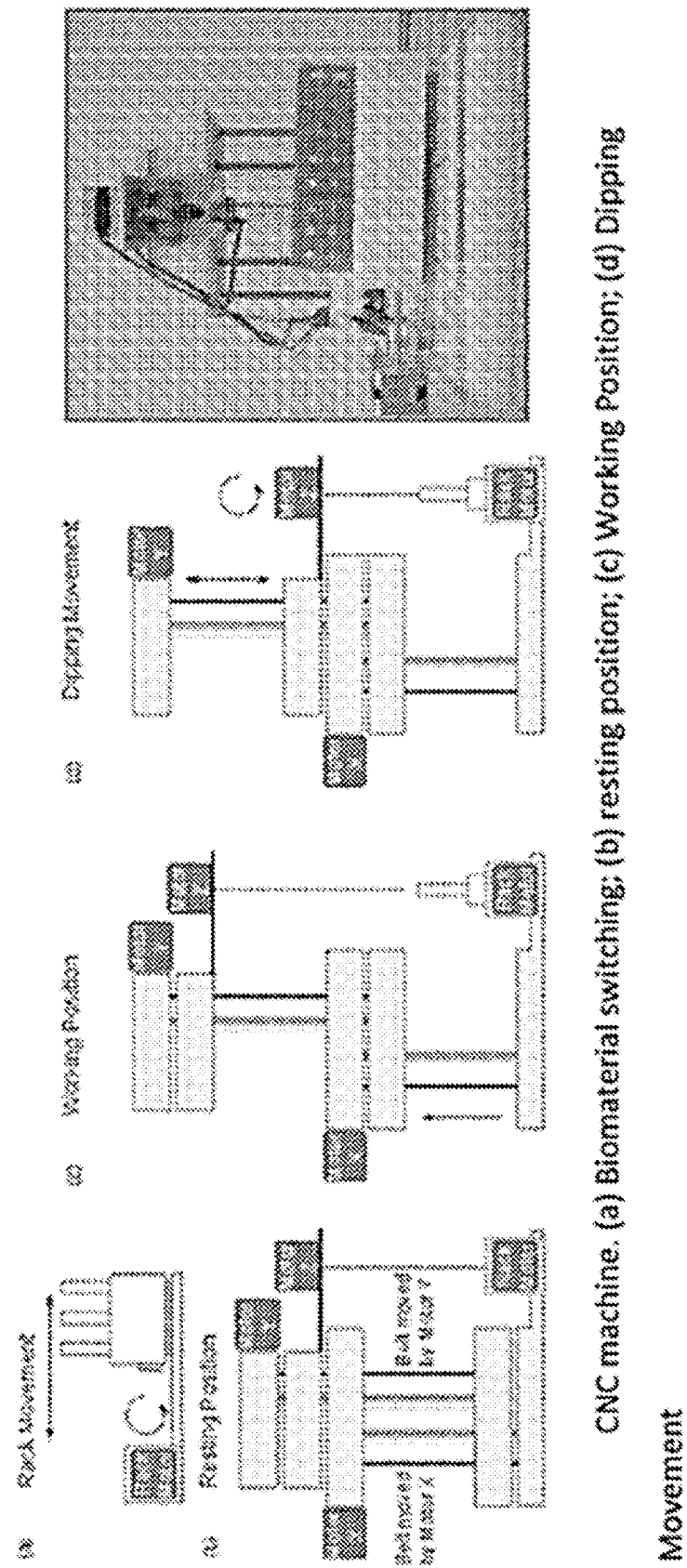
FIG. 1: Computerized numerical control (CNC) machine.

The present invention solves the technical problem of providing a method to produce a multilayer hollow tube which can be produced easily and rapidly and has the further advantage that its structure mimics that of natural part of the body. Hence it can advantageously be used in many biomedical applications, such as, for example, blood vessel, urethra allograft and prostate allograft. Indeed, it has now surprisingly be found that when the crosslinking or polymerization of the functionalized gelatin is performed while the rod is rotating and emerging from the pre-polymerized solution the gelatin fibers forming the layers are aligned in a manner similar to the collagen's natural alignment. Due to the alignment of the fibers, the multilayer hollow tubes are permeable to the substances normally present in the body. Hence, if the pre-polymerized solution also comprises cells, such as mature or differentiated cells (for example endothelial cells) or mesenchymal stem cells, said cells are still able to proliferate and differentiate, and are aligned so as to confer to the tubes a less thrombogenic luminal surface configuration. The cylindrical construct with multiple multilayers encapsulating cells and/or protein factors and/or other components as explained in more details below may serve as a guide axonal regeneration of a central or peripheral nerve.

The method according to the present invention provides the step of: i) dipping a rod, which can be made of any material, such as plastic or metal, and can have any diameter, into a pre-polymerized solution comprising gelatin and a photo-initiator, the gelatin being chemically functionalized to become reactive to polymerization or crosslinking in presence of free radicals; ii) exposing the pre-polymerized solution attached to the rod to light, visible light, UV light or infrared depending on the nature of the photo-initiator while the rod is rotating and emerging from the pre-polymerized solution to obtain a polymerized or crosslinked layer; and iii) repeating steps i) and ii) to obtain the desired number of layers. The pre-polymerized solutions used for each layer can have the same or different compositions.

Preferably, the pre-polymerized solution comprises a UV photo-initiator which leads to cross-linking of the functionalized gelatin after exposure to UV light.

The pre-polymerized solution is a solution comprising a polymer which has not yet been polymerized or crosslinked. More specifically, the pre-polymerized solution comprising functionalized gelatin is a solution comprising functionalized gelatin.

The amount of functionalized gelatin can be in the range of 1-20% w/v, preferably 8-12% w/v and even more preferably 10% w/v based on the total amount of pre-polymerized solution.

The functionalized gelatin is a gelatin, the amino acidic chain of which is functionalized with a chemical agent selected from the group consisting of methacryloyl groups, acryloyl groups or any functional group or a moiety capable of mediating formation of a polymer or reaction with a surface or other molecule. Functional groups include the various radicals and chemical entities taught herein, and include alkenyl moieties such as acrylates, methacrylates, dimethacrylates, oligoacrylates, oligomethacrylates, ethacrylates, itaconates or acrylamides. Further functional groups include aldehydes. Other functional groups may include ethylenically unsaturated monomers including, for example, alkyl esters of acrylic or methacrylic acid such as methyl methacrylate, ethyl methacrylate, butyl methacrylate, ethyl acrylate, butyl acrylate, hexyl acrylate, n-octyl acrylate, lauryl methacrylate, 2-ethylhexyl methacrylate, nonyl acrylate, benzyl methacrylate, the hydroxyalkyl esters of the same acids such as 2-hydroxyethyl acrylate, 2-hydroxyethyl methacrylate, and 2-hydroxypropyl methacrylate, the nitrile and amides of the same acids such as acrylonitrile, methacrylonitrile, and methacrylamide, vinyl acetate, vinyl propionate, vinylidene chloride, vinyl chloride, and vinyl aromatic compounds such as styrene, t-butyl styrene and vinyl toluene, dialkyl maleates, dialkylitaconates, dialkyl methylene-malonates, isoprene, and butadiene. Suitable ethylenically unsaturated monomers containing carboxylic acid groups include acrylic monomers such as acrylic acid, methacrylic acid, ethacrylic acid, itaconic acid, maleic acid, fumaric acid, monoalkylitaconate including monomethyl itaconate, monoethylitaconate, and monobutylitaconate, monoalkyl maleate including monomethyl maleate, monoethyl maleate, and monobutyl maleate, citraconic acid, and styrene carboxylic acid. Suitable polyethylenically unsaturated monomers include butadiene, isoprene, allylmethacrylate, diacrylates of alkyl diols such as butanedioldiacrylate and hexanedioldiacrylate, divinyl benzene, and the like. It is preferred that the amino acidic chain is functionalized with methacryloyl groups to give methacrylated gelatin.

The degree of functionalization of the acidic side chain of the gelatin polymer with a chemical agent capable of polymerizing or crosslinking in presence of free radicals is from 10% to 100%, preferably from 20% to 100%, more preferably from 30% to 100%, more preferably from 40% to 100%, more preferably from 50% to 100%, more preferably from 60% to 100%, more preferably from 70% to 100%, more preferably from 80% to 100%, more preferably from 90% to 100%. The amino acids involved in the functionalization can be one or more selected from the group consisting of serine, threonine, arginine tyrosine, lysine and others. Preferably, the functionalized amino acid is the lysine residue.

Usually, the temperature of the pre-polymerized gelatin solution in step i) is from 26 to 40° C., preferably from 28 to 37° C. and more preferably 37° C. Different temperatures can also be used depending on the type of the functionalized gelatin used. Indeed, as specified throughout the description the pre-polymerized composition comprising gelatin has to be a solution. Thus, the skilled person will be able to set the temperature without undue burden.

A photo-initiator is a chemical compound or molecule that after light stimulation or application, covalent bonds break forming one, two or more radicals to assist radical polymerization. Suitable photo-initiators useful in the present invention are well known in the art. Camphorquinone, Irgacure, Darocure etc. may be mentioned just as an example but suitable photo-initiator are not limited to these compounds. Suitable amounts of photo-initiator in the pre-polymerized solution are from 0.1 to 10% w/v. In some cases the amount of photo-initiator is from 0.1 to 1% w/v, more preferably from 0.2 to 0.5% w/v.

The pre-polymerized solution can further comprise alginate or salts thereof or derivatives thereof. Suitable salts include, for example, sodium, potassium and lithium. The presence of these compounds can induce variation in the viscosity of gelatin which in turns influences the thickness of the layers. Hence, by selecting the amount of alginate in the pre-polymerized solution it is possible to increase and select the desired thickness of the layers. Layers of polymerized gelatin without alginate can be as thin as 1 µm. The addition of alginate, salts or derivatives thereof, to the pre-polymerized solution allows to produce layers having a thickness up to 400 µm.

The pre-polymerized solution can comprise from 0.005% to 5% w/v alginate or salts thereof or derivatives thereof, preferably from 0.15% to 2% w/v, even more preferably from 0.15% to 1.5% w/v or from 0.3% to 0.6% w/v.

The pre-polymerized solution according to the present invention can further comprise at least one compound selected from the group consisting of gelatin chitosan, gellam gum, collagen, elastin, cellulose mixtures thereof, salts thereof and derivatives thereof. Further, pre-polymerized solution can also comprise at least one selected from viable cell, proteins, drugs and polymeric particles. Preferable cells are mature or differentiated cells, such as endothelial cells, or mesenchymal stem cells but other types of cells can also be used. Polymeric particles are micro or nano particles that can contain other elements for control release of those. Basically a particle is a nano or micro-bead or particles compose of any polymeric compound capable to encapsulate other type of compounds, typically with biological activity.

The multilayer hollow tubes can also be obtained using a pre-polymerized solution that comprises 1 to 2% w/v of chitosan, preferably 1% w/v of chitosan. The pre-polymerized solution of chitosan can additionally comprise at least one compound selected from gelatin, gellam gum, collagen, elastin, cellulose, viable cells, proteins, drugs and polymeric particles. Preferably, the pre-polymerized solution comprising chitosan also comprises endothelial cells and/or mesenchymal stem cells. When chitosan is used in the pre-polymerized solution, the polymerization is obtained by means of a gelling agent. Usually the gelling agent is a solution comprising 2 to 6% w/v, preferably 4% w/v of a gelling compound, such as tripolyphosphate.

In a preferred embodiment, at least one of the layers of the multilayer hollow tube is coated with polymer fibers. Suitable polymers are for example gelatin, degradable poly(ester carbonate urethane)urea (PECUU) and poly(carbonate urethane)urea (PCUU) and polycaprolactone. Preferably, polycaprolactone fibers are applied. The fibers may have a diameter ranging from 10 µm to 100 nm. Preferably, from 10 µm to 300 µm. The fibers, such as for example the polycaprolactone fibers, can coats the multilayer hollow tube, i.e. the external layer of the tube comprises polycaprolactone fibers or can coat just one of the layers of the multilayer hollow tube, i.e. the fibers are present between two layers of hydrogel. The presence of spun of fibers, such as polycaprolactone fibers, provides structural support to the multilayer hollow tube. The fibers are applied by solution blow spinning (SBS) which is a technique known in the art. When polycaprolactone is used for the coat this can have an average molecular weight Mw from 5000 to 110000 Da, preferably from 50000 to 95000 Da and even more preferably from 60000 to 85000 Da. The solution of the polycaprolactone used for the SBS can comprise from 1% to 30% w/v of polycaprolactone, preferably 1% to 20% w/v and even more preferably from 7% to 15% w/v. Suitable solvents for the polymer solution to be applied by SBS solution includes all solvents in which the polymers are soluble. For example, when polycaprolactone fibers have to be applied, the polycaprolactone can be dissolved in a mixture of acetone and chloroform. Suitable amount can be for example acetone/chloroform 20%/80%. However, other solvents and mixture of solvents in variable amounts can also be used.

The injection rate of the solution in the SBS step can be, for example, from 40 µL/min to 350 µL/min, preferably from 80 µL/min to 250 µL/min and even more preferably from 120 µL/min to 200 µL/min. However, also different injection rates can be applied. The air pressure in the SBS step can be, for example, from 10 psi to 120 psi, preferably, from 20 psi to 100 psi, more preferably from 30 psi to 80 psi and even more preferably from 40 psi to 60 psi. However, also different values of air pressure can be applied.

In some cases it may be advantageous to add an alginate layer before applying the polymer fibers, such as the polycaprolactone fibers, by solution blow spinning. This is because a layer of alginate between the layer of polymerized gelatin (i.e. the hydrogel) and the polymer fibers may prevent drying of the polymerized gelatin (i.e. the hydrogel). The drying of the hydrogel layer may also depend on the air stream applied during SBS. The conditions to be used in order to obtain an alginate layer in the multilayer hollow tube will be explained below with reference to the conditions for the alginate solution to be applied to the rod, i.e. the conditions and the preferred embodiments are the same.

In some embodiments the pre-polymerized solution comprises 10% w/v of methacrylated gelatin (such as bovine methacrylated gelatin, GelMa), 0.5% w/v of sodium alginate, 0.2% w/v of photo-initiator (such as 1-[4-(2-hydroxyethoxy)-phenyl]-2-hydroxy-2-methyl-1-propane-1-one (Irgacure 2959) and encapsulated cells; and the multilayer tube is coated with polycaprolactone fibers by means of SBS using a solution comprising 7% w/v of polycaprolactone.

There are two ways to construct the grafts. One way is to construct each layer as a combination of a sub-layer of functionalizedgelatin, and photo-initiator (and optionally alginate, salts or derivative thereof) and a sub-layer of polycaprolactone fibers. The other way is to construct each layer as a combination of numerous intercalated microlayers of functionalized gelatine and photo-initiator (and optionally alginate, salts or derivative thereof) and microlayers of polycaprolactone fibers. The number of layers and SBS time depends of the application.

In order to easily remove the multilayer hollow tube from the rod a soft hydrogel lumen structure fabricated from a sacrificial material can be used since it reduces or eliminates the friction force during removal. This can be particularly advantageous when the first layer (i.e. the luminal layer) of the tube comprises encapsulated cells.

Therefore, in one aspect of the present invention the method provides an additional step to be performed before the step i) above in which the rod is dipped at least once in a solution comprising alginate or salts thereof or derivatives thereof; and then dipped in a solution inducing polymerization or crosslinking of the alginate or salts thereof or derivatives thereof.

Conditions for the Alginate Solution to be Applied to the Rod.

The alginate solution can comprise from 0.025% to 3% w/v of alginate, salts or derivatives thereof. Suitable salts are for example sodium, lithium and potassium. Preferably, the alginate solution comprises 2% of alginate, salts or derivatives thereof. The solution preferably has a viscosity of 6 cPs (centipoises) to 245 cPs. For the viscosity measurements, the prepared solutions were equilibrated between 20 and 25 minutes at 37° C. before measurement. An Anton Paar MCR 301 rheometer equipped with a cone-plate geometry (plate diameter of 50 mm and cone opening angle of 0.5°) was used to investigate the shear rate dependence of the solution viscosity. A shear flow test with shear rate ramp from 10 to 1000 $s^{-1}$ was performed at 37° C. Viscosity data shown in this work is obtained at a shear rate of 100 $s^{-1}$.

As a solution suitable to crosslink or polymerize alginate or salts thereof or derivatives thereof, any solution comprising $Ca^{+2}$, $Ba^{+2}$, $Sr^{+2}$, $Fe^{+3}$, $Al^{+3}$ and the like can be used. Some examples include $CaCl_2$, $CaSO_4$, $CaCO_3$ etc. Preferably, said solution comprises $CaCl_2$. Suitable amount of these compounds in the polymerizing solution are from 1% to 20% w/v, preferably from 2% to 10% w/v and even more preferably 4% to 6% w/v.

After dipping in the polymerization solution the rod coated with alginate can be immersed in a cleansing solution, such as a PBS solution, to remove the polymerization reagent. Optionally, the rod coated with alginate can be subjected to successive dipping rounds wherein the successive dipping rounds comprise:
a) a first round of two dipping in the alginate solution followed by dipping in the polymerization solution and, optionally, in the cleansing solution; or
b) 1, 2, 3 or 4 dipping in the alginate solution followed by dipping in the polymerization solution and, optionally, in the cleansing solution.

Preferably, the dipping upwards-speed when dipping the rod in the alginate solution is 138 m m/s.

The multilayer hollow tubes of the present invention have a lumen diameter of at least 1.5 mm, preferably from 1.5 mm to 1.5 cm, more preferably 1.5 mm to 1 cm, more preferably 1.5 to 6 mm, more preferably from 2 to 6 mm and even more preferably of 4 mm. Each layer of the tube has a thickness of 1 to 400 µm, preferably 1 to 250 µm and comprises polymerized or crosslinked chemically functionalized gelatin. The gelatin can be derived from any sources such as for example animal and fish.

The layers of the multilayer hollow tubes of the present invention can have the same compositions or have different compositions from one another. Additional components that can be present in the layers are gelatin, alginate, chitosan, gellam gum, collagen, elastin salts and derivatives thereof, viable cells, proteins, drugs and polymeric particles. Preferably at least one of the layers comprises cells and more preferably the cells are selected from endothelial cells or mesenchymal stem cells. To increase structural tensile strength of to the multilayer hollow tube it can be advantageous that at least one of the layers is coated with polymer fibers (as explained above).

The multilayer hollow tubes according to the present invention can be used in many biomedical applications and some examples include blood vessel graft, urethral graft prostate graft and any kind of implantable prosthesis.

As explained above, if the pre-polymerized solution also comprises endothelial cells or mesenchymal stem cells, preferably the layer comprising the cells is the first layer which is in contact with the lumen of the tube. In preferred embodiments, the multi-layer tube comprises at least a layer of encapsulated cells in polymerized or crosslinked gelatin (or chitosan as explained above) to provide biological functionality and at least one of the layers is coated with polycaprolactone fibers to give structural support. After preparation of the layers the tube can be removed from the rod using any known technique in the art.

The present invention will now be described with reference to some explicative examples which however are not intended to limit the scope of the invention.

EXAMPLES

Example 1

Robotic Device

A computerized numerical control (CNC) machine that allows the controlled elevation, drop and rotation of a metal mandrel was designed and constructed in our laboratory and it is illustrated in FIG. 1. The robot consists of several platforms that can slide vertically, guided by steel rod, and moved by pulleys, belts and 2 NEMA 16 stepper motors (SM-42BYG011-25, Mercury Motor, China). The first motor, denominated as Motor X, allows the system to go from rest position (FIG. 1(b)) to working position (FIG. 1(c)); whereas the second motor, Motor Y, controls the mandrel dipping while the rotational movement is performed by a third NEMA 16 stepper motor, Motor Z, shown in FIG. 1(d).

Motors are controlled by an electronic circuit using different Open Source elements. The hardware consists of an Arduino UNO R3 microprocessor (50, Adafruit, USA) connected to a gShield v.5 (1750, Adafruit) specially designed to allow easy control of 3 bipolar stepper motors simultaneously. The CNC machine is controlled by the Grbl firmware, which is a high performance program code for controlling the motion of stepper motors that run on the Arduino-gShield circuit. G Code command inputs are streamed to the circuit using the Universal G-Code Sender. Additionally, a moving rack system is included to allow interchange of biomaterial during multi-material based graft fabrication, and a suitable light source, such as for example UV lights source (365 nm), to induced photo-crosslinking of specialized biomaterials. Both systems are controlled by a second Arduino UNO R3 microprocessor which is coordinated using inputs from the first Arduino. Rack movement uses a Bigeasydriver (ROB-10735, SparkFun Electronics, USA) to run a fourth stepper motor (see FIG. 1(a)), and the light switching, such as for example a UV light switching, is handled directly through the outputs commanding of the second Arduino. Commands for the rack and lights are directed using the Arduino sketch software.

Hydrogels (i.e. Pre-Polymerized Solutions)

Alginate solutions were prepared at different concentration in PBS IX using medium viscosity alginate (A2033, Sigma, USA). After dissolving alginate under vigorous stirring at 70° C., solutions were filtrated through a 0.45 µm syringe filter before use.

Methacrylated gelatin, or GelMa, was synthesized after mixing methacrylic anhydride, and reacting with amino groups from a gelatin solution as previously described. Briefly, bovine gelatin (Bloom 220, Rousselot, Netherlands) was dissolved to a final concentration of 10% (w/v) in PBS IX (pH 7.4) at 60° C. After fully dissolved, while still stirring, methacrylic anhydride (276685, Sigma, USA) was added slowly to a final concentration of 8% (v/v). After 3 hrs of reaction, 5× dilution in PBS IX was performed and the reacted gelatin dialyzed against deionized water at 40° C. for 1 week. Daily replacements of fresh deionized water were done to remove all unreacted methacrylic anhydride. Finally, the dialyzed mixture was freeze dried before storage. To promote free radical polymerization of GelMa in solution, a photo-initiator (PI) was used to a final concentration of 0.5% (w/v). The 5% (w/v) PI stock solution was prepared by dissolving 2-Hydroxy-4'-(2-hydroxyethoxy)-2-methylpropiophenone (410896, Sigma, USA) in PBS IX and heated to 70° C. until fully dissolved. Fresh pre-polymerized solutions were prepared for each experiment and the basal GelMa solution was consisted of 10% (w/v) methacrylated gelatin and 0.5% (w/v) PI in PBS IX. To improve transparency, small precipitant were removed after filtering through a 0.45 µm syringe filter.

Chitosan solutions were prepared at different concentrations after dissolving chitosan (44887, Sigma, USA) in a 1% (v/v) acetic acid solution (537020, Sigma, USA) to a final concentration of 2% or 1% (w/v) and filtered through a 0.45 µm syringe filter before use. The TPP solution for chitosan ionic gelation during immersion was prepared by dissolving sodium tripolyphosphate (72061, Sigma, USA) in ddH$_2$O to a final concentration of 4% (w/v).

Lumen Structure

The strategy used for the hollow lumen formation is through the disposition of layer around an alginate-based mandrel of 2-6 mm in diameter, which after alginate dissolution the remaining cylindrical structure would contain an emptied centric region mimicking the luminal section of vascular vessels.

These alginate mandrels with controllable diameter were built after dipping a thin metal mandrel of 0.5 mm in diameter in a tube with dissolved alginate, then submerged during 15 s in a 5% (w/v) CaCl$_2$ solution (06991, Sigma, USA) for polymerization and finally immersed in PBS for 1 min for cleansing. To fabricate structures with larger diameters successive dipping rounds were performed. The first round always consisted of 2 dippings in alginate solution, polymerization and a PBS washing, whereas the successive rounds consisted either of 1, 2, 3 or 4 alginate dippings, polymerization and PBS washing. Each mandrel structure obtained with different combination of fabrication parameters were repeated 3 times for statistical analysis. In order to observe the structural homogeneity along the construct, the total length was divided in three different sections of equal length, and defined as front, mid and tail. Head section as illustrated in FIG. 2(a)(left) is removed and not considered for vessel graft fabrication.

Layers

Figure 2:
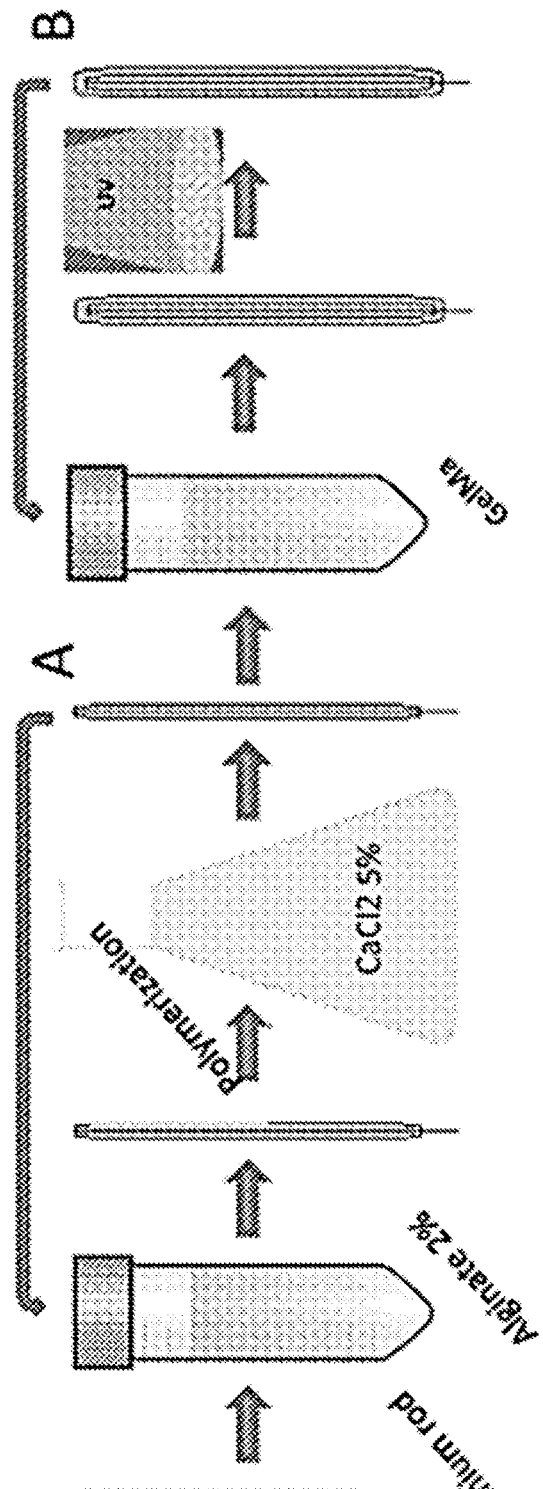
FIG. 2: A) Alginate dipping/polymerization; B) GelMa (manufactured by Khademhosseini Lab; this material is a porcine gelatin skin functionalized with methacryloyl groups mainly at the side chain of lysine, but also other amino acid residue can be functionalized) dipping/polymerization.

Layers of gelatin were generated through the dipping of a metal rod harboring around a previously constructed alginate mandrel, in a solution of 10% (w/v) GelMa, 0.5% (w/v) photo-initiator (PI), with or without supplemented alginate at different concentrations (see FIG. 2(B)). Alternatively, HUVEC cells or 1 Hg/mL BSA-FITC (A9771, Sigma, USA) were added to the pre-crosslinked solution in order to obtain cellularized or fluorescent layers respectively. Solutions were kept in a water bath at 30° C. to avoid spontaneous gelation at room temperature. Crosslinking was achieved by exposing the gelatin solution to UV light at 365 nm wavelength (261 mW/cm$^2$) (OmniCure* S2000, Excelitas Technologies, USA) from a distance of 2 cm while the coated mandrel was rotating and emerging from the pre-crosslinked solutions.

Chitosan (CS) layers were fabricated after dipping the resultant alginate rod twice in a chitosan solution and once in TPP for 15 s to promote ionic polymerization and washed in PBS IX for 1 min afterward.

Cell Culture

HUV-EC-C [HUVEC] (ATCC® CRL1730™) cells were cultured in high glucose Dulbecco's Modified Eagle Medium (10313, Gibco, USA) supplemented with 2 mM glutamine (25030-081, Gibco, USA), 10% fetal bovine serum (16000-044, Gibco, USA) and 1% penicillin-streptomycin (15140-122, Gibco, USA).

Cultures were maintained in an incubator at 37° C. and 96% humidity with 5% $CO_2$ enriched air atmosphere. Cells were maintained changing fresh media every 2-3 days and passaged when 80% cell confluence is reached.

Proliferation and Viability Testing

Cell proliferation assessment of encapsulated HUVEC in the crosslinked biomaterials were performed using the WST-1 Cell Proliferation Colorimetric Assay Kit (K302, Biovision, USA) following the manufacturer instructions. Briefly, this assay quantifies the metabolic cleavage of WST-1 to generate formazan by cellular mitochondrial dehydrogenases. On the other hand, cell viability of encapsulated HUVECs was measured using the LIVE/DEAD® Cell Imaging Kit (488/570) (R37601, Thermo Fisher Scientifics, USA).

Image Analysis

Image analysis to determine structures' dimensions, such as length and width, were performed using the open source and Java-based imaging program ImageJ (National Institutes of Health).

Statistical Analysis

Data are presented as means±standard deviation. Differences between means were tested by Student's t-test. A probability level of $P<0.05$ was considered to be significant.

Results

Lumen Structure

In order to standardize luminal diameter of SDBV using the strategy of sacrificial alginate mandrel, and to determine the most suitable parameters that control the diameter and lumen dimensional uniformity, several optimization were implemented. This included the quantification of the effect of alginate concentration, the number of dippings and the mandrel upward-speed during emersion from the pre-polymerized alginate solution, in the process of alginate mandrels fabrication.

The studied range of alginate concentration spans between 1% to 3% (w/v) with interval of 0.5% increments, dippings from 1 to 4 before polymerization and upward-speed from 4.6 to 184 mm/s. FIG. 3(a) illustrates the morphology and shape variation of the alginate mandrel throughout its different sections. Each of these sections was considered for dimensional analysis.

Structures fabricated with alginate concentrations below 2% (w/v) at any upward-speed below 23 mm/s were highly irregular and not suitable for analysis. Visual inspection of these constructs indicates that while working under those parameters, the slight vibration of the CNC machine has a negative effect on the structural regularity inducing a rippled pattern.

Figure 3:
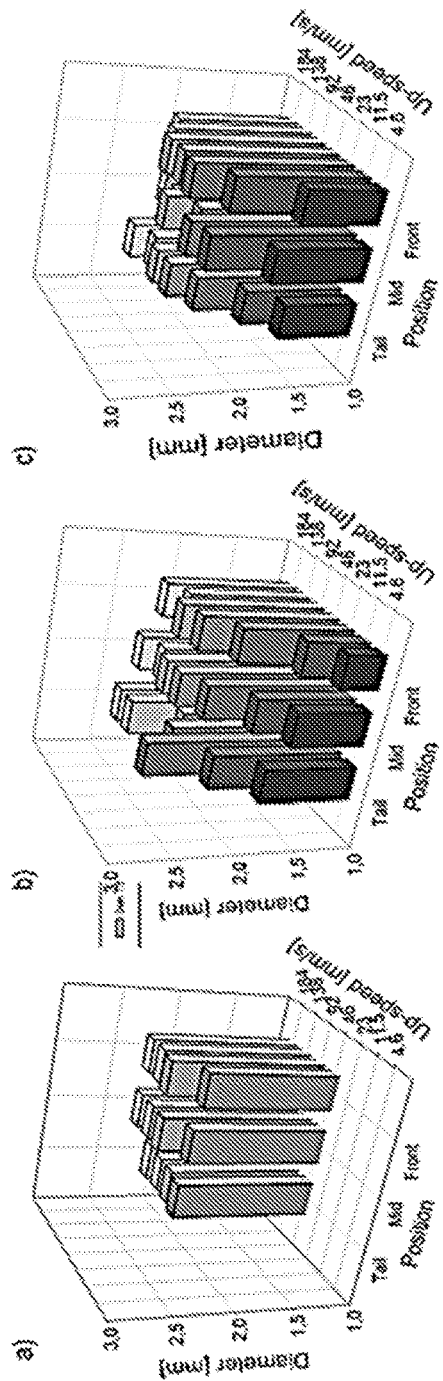
FIG. 3: a) (left) Picture of a 2% alginate lumen structure identifying its head, front, mid and tail; a) to c) Lumen structures diameters at different concentrations of alginate. Representation focuses on comparisons of lumen or alginate mandrel dimensions at the different sections (front, mid and tail).
Figure 3:
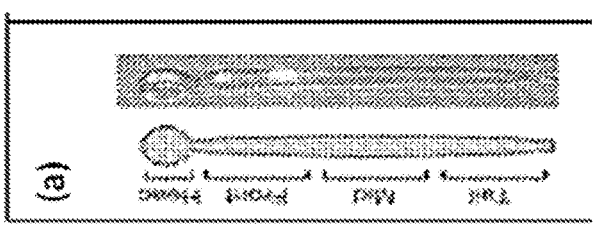

FIG. 3 shows the diameter of alginate structures at the front, mid and tail sections after a first round of alginate deposition at different concentrations of alginate and mandrel's upward-speed. An overall analysis of the graph indicates that diameter expands together with upward-speed increments, reaching its maximum value at a speed about 92 mm/s, which then turn to get smaller as the emersion speed keep raising. Examining the results for each alginate concentration separately, it is possible to observe that mandrel structures fabricated with 2% (w/v) alginate are the most uniform, characterized by similar diameter values among front, mid and tail sections, with no significant difference between those values at any speed. Whereas most 2.5% (w/v) alginate constructs show diameters increment going from mid to tail, presenting statistical differences in average diameters between these two sections. For the 3% (w/v) alginate structures, which appear to be the most irregular ones, significant differences are observed when comparing all different sections.

These results indicated that 2% (w/v) alginate and 138 mm/s upward-speed is the most suitable parameters to obtain uniform structures; therefore, additional alginate layers, at different alginate concentrations, were added using the 138 mm/s upward-speed in order to further increase the alginate mandrel diameter while keeping homogeneous dimensions at the different sections.

Figure 5:
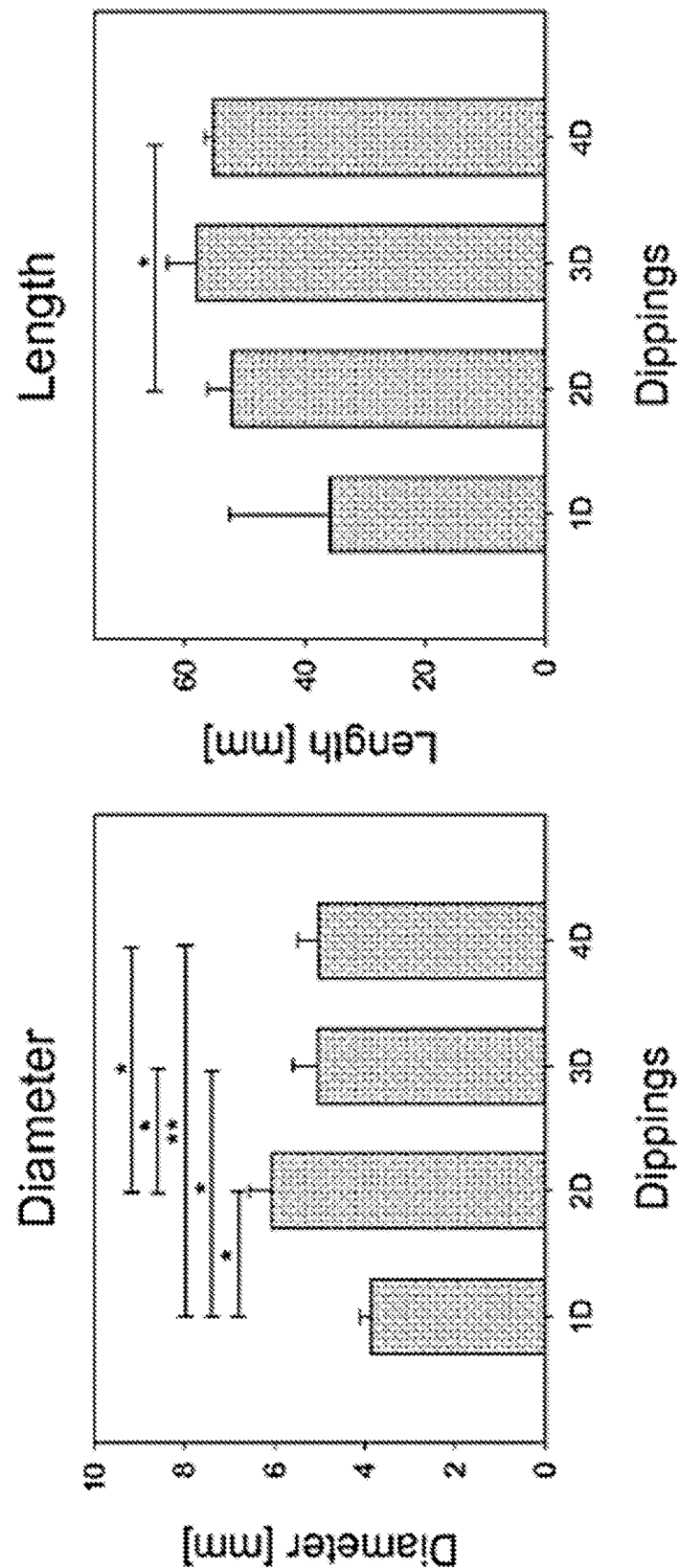
FIG. 5: Lumen structures' average diameter between front and mid and length; the structures were constructed using 3 rounds of dipping/polymerization. Dips were performed into 2% (w/v) alginate solutions and with 138 mm/s as upward-speed. For all constructs the first round was done with 2 dippings before polymerization and the second with 4 dippings. The Figure shows the results for the third round using 1, 2, 3 or 4 dips before polymerization.

FIG. 5 shows the diameter and length of lumen structures fabricated after adding alginate concentric layers over the previously first optimized alginate structure.

The useable length is calculated after measuring the diameter every 0.25 mm along the alginate mandrel. From a middle point toward the front section the accumulated average diameter is calculated, and if the next diameter, when subtracted to the average value, the different is equal or higher than 0.5 mm, the front useable limit is establish. The same procedure applies for the tail limit, and the distance between the front and the tail limit correspond to the useable length. Concentric layers were added by dipping the alginate mandrel 1, 2, 3 or 4 times in a 1, 1.5 or 2% (w/v) alginate solution before polymerization. In general, the obtained structures presented small differences in diameter between front, mid and tail sections, therefore the observed diameter values in FIGS. 4 and 5 correspond to the mean diameter along the different sections. It is possible to observe that additional dipping before polymerization did not necessarily increase the structures' diameter or length but reduced the standard deviation of the mean length. Additionally, there is no significant difference in the diameter of constructed mandrels using 3 and 4 dips of 1% and 1.5% (w/v) alginate before polymerization. In contrast, structures obtained after using 1, 2, 3 or 4 dips of 2% (w/v) alginate are significantly thicker than those with less alginate concentration, reaching a maximum of 4.3 mm with 1 dip. Lastly, 4 dips of 2% (v/w) alginate before polymerization appear to be the best setting because of the small standard deviation in diameter and length.

To achieve a final diameter of 6 mm, which is the upper range limit for coronary arteries, a third round of alginate dipping and polymerization was performed. Considering the previous results, testing of the number of dippings before polymerization was done using only alginate 2% (w/v) and 138 mm/s upward-speed, since it corresponded to the optimal settings for previously constructed alginate layers. Interestingly, the double dipped structures in the third round of dipping/polymerization showed an average diameter of 6 mm and 50 mm in length as depicted in FIG. 5. As discussed above, this data does not reveal any correlation between structure diameter or length and the number of dipping before polymerization, but as dipping number increases, the structures' dimensions has lower standard deviation, especially in length.

Layers

Natural blood vessel's structure consists of a series of layers with different widths, cellular content and extracellular matrix composition, therefore in this work; we explored the control in thickness for layers generated with different biomaterials and cellular content.

GelMa-Alginate Layer

Figure 6:
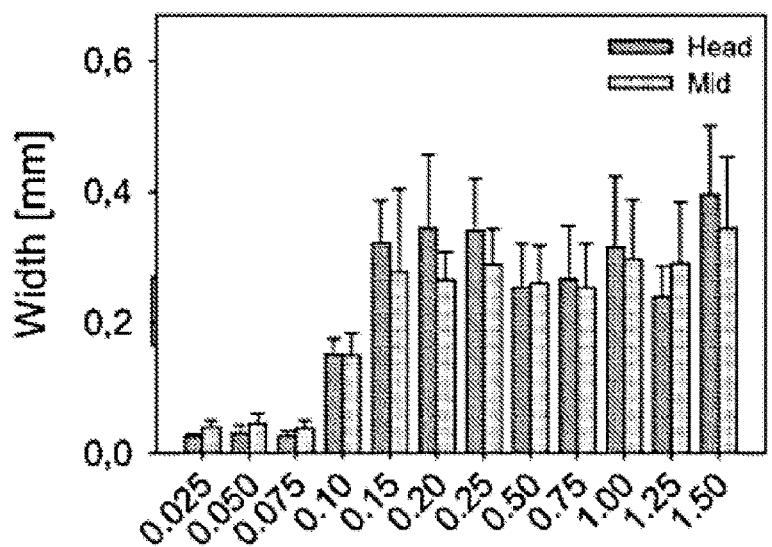
FIG. 6: Effect of alginate content on the width of gelatin layers. * $p<0.05$;  $p<0.005$; * $p<0.001$.

10% (w/v) GelMa solution supplemented with variable concentrations of alginate were prepared as described in the materials and methods section, and layers were deposited over an alginate mandrel structure obtained from one round of dippings and polymerization (2 dippings, 2% (w/v) alginate and 138 mm/s upward-speed). Variable concentrations of alginate were tested in order to obtain a GelMa solutions with a viscosity range, and to test the effect of viscosity in the control of layer width. Average width of layers obtained at different concentration of supplemented alginate at the front and mid sections are shown in FIG. 6 (in terms of diameter, tail and mid sections were not distinguished, and then considered as a unique section). Within a low range of alginate concentrations, ranging from 0.025% up to 0.075% (w/v), no statistical differences in width were observed (~0.04 mm), and the standard deviations were maintained at lower values. However, a rapid increment in width is observed (up to ~0.3 mm) when 0.075% to 0.15% (w/v) alginate concentrations were tested. In contrast, the statistical differences were lost for ranges standing above (0.15% to 1.5% w/v). In summary, thicknesses at low alginate concentrations are statistically different from those using high alginate content, however the fine tuning in vessel thickness is only possible within the short range from 0.075% to 0.15% (w/v) of alginate when supplemented in the 10% (w/v) GelMa solution. Due to the crosslinking of layers are induced simultaneously during emersion, and immediately after every section of the cylindrical graft is egressing from the uncrosslinked solution, upward-speed was fixed at 6.9 mm/s and rotational speed of the mandrel at 42 rpm for homogeneous UV irradiation.

Chitosan Coating

The effect of chitosan concentrations and the upward-speed on the final deposition of polymerized chitosan were assessed by measuring the width of concentric chitosan layers encircling the alginate mandrel fabricated previously. To describe the chitosan concentration effect, 1%, 1.5% and 2% (w/v) chitosan solutions were used at a fixed upward-speed of 138 mm/s. The effect of upward-speed over width was evaluated fabricating chitosan layers using a fixed concentration of 1% (w/v) and two different upward-speeds ranging from 23 mm/s to 138 mm/s. Finally, due to lack of transparency of chitosan layer, widths were calculated as half the difference between the diameter of the alginate mandrel and the resulting diameter of the whole construct, including the alginate mandrel and the layer as shown in FIG. 7(a).

Figure 7:
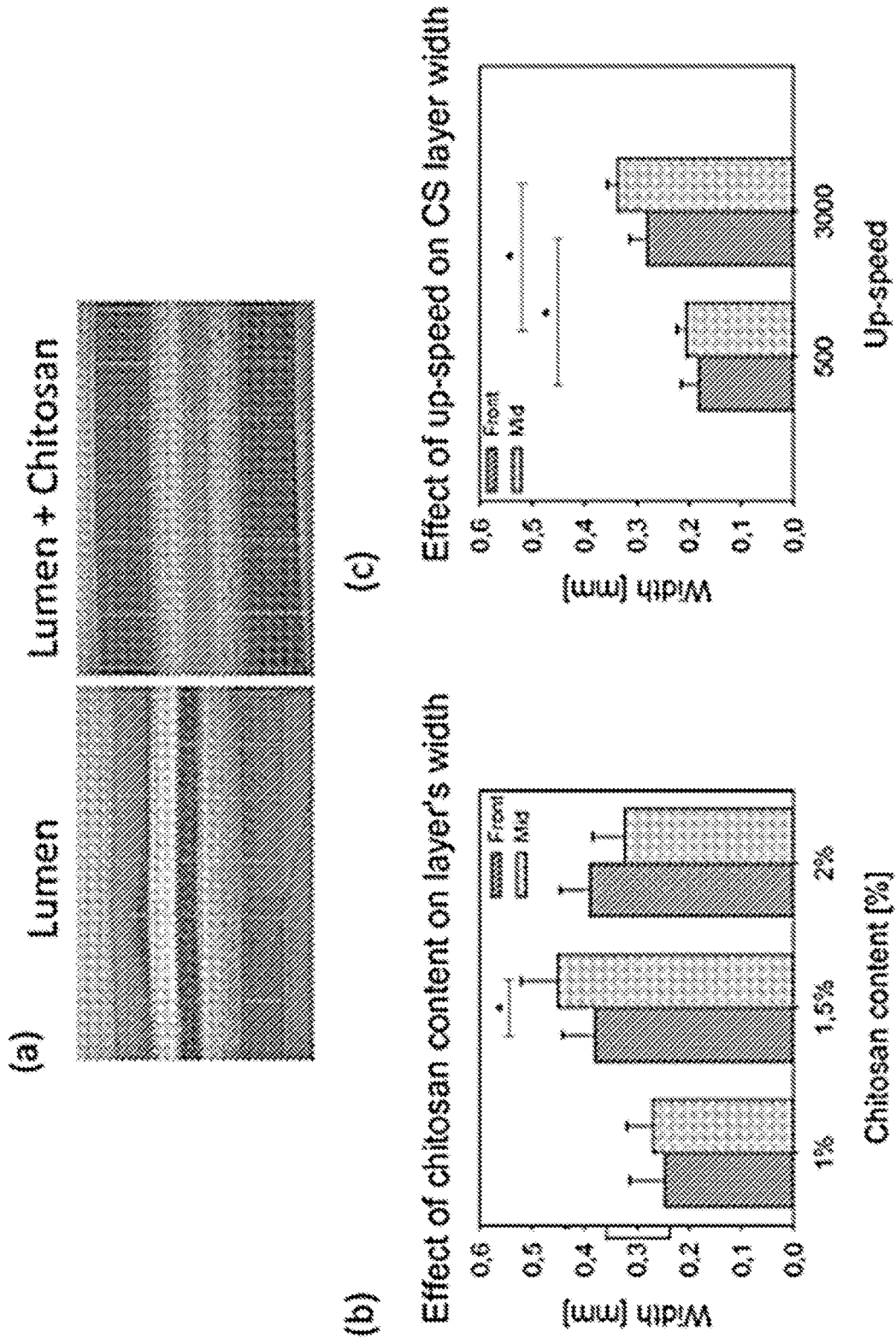
FIG. 7: Chitosan layer experiments, a) Chitosan layers' width was determined after subtracting to a Lumen+Chitosan diameter the value of the lumen's diameter and dividing by 2. b) Effect of chitosan concentration on the layers width, c) Effect of upward-speed on chitosan layer's width.

The concentration effect (FIG. 7(b)) and the influence of upward-speed on the layer's width in the front and middle sections measurements (FIG. 7(c)) show no obvious correlation between the studied parameters and the level of deposited material at any point of the construct. Nevertheless, layers of 1% w/v in chitosan content showed more dimensional similarity between the front and mid sections, making this concentration more appropriate to construct multilayer structures with uniform metrical properties along its length. A similar analysis indicates 23 mm/s and 138 mm/s upward-speed as right fabrication parameter since the resulting structure in both cases does not show any dimensionally significant difference at the front and middle section.

Similarly to alginate, viscosity increments has the tendency to generate thicker concentric layers, however above certain limit (corresponding viscosity to 1.5% chitosan), this correlation is lost. On the other side, and similarly to alginate, there is a positive proportionality between upward-speed and layer width. Hence, the introduction of a different biomaterial such as chitosan can be also adapted to generate concentric multilayers with controllable thickness as shown for alginate and gelatin.

Cell Encapsulation.

Functional SDBV grafts can only be achieved with in the presence of the appropriate cellular contents that are normally found in natural vessel structures. Therefore we investigated the feasibility of adding concentric multilayers of cell-laden hydrogel using the automatized system. In order to achieve this, HUVECs (endothelial cells) were added to a final concentration of 4, 6 and $8\times10^5$ cells $mL^{-1}$ in 10% (w/v) GelMa, 0.5% (w/v) PI and 0.5% (w/v) alginate solution; the layer was formed after one round of dipping of the previously formed alginate mandrel into this solution and crosslinking with UV irradiation. UV crosslinking was performed using an emersion speed of 6.9 mm/s and a rotational speed of the mandrel of 42 rpm.

Figure 8:
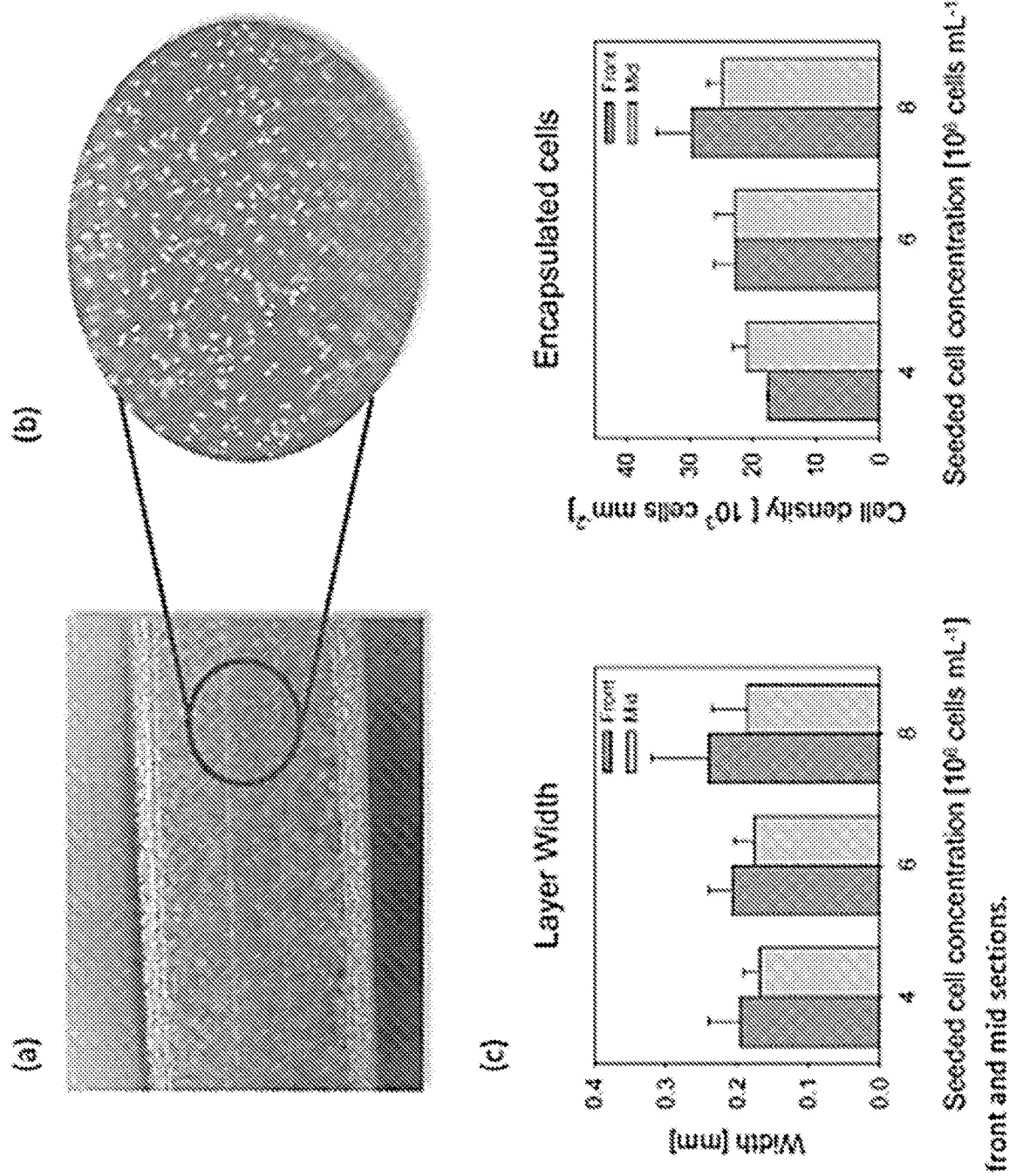
FIG. 8. Cellularized layer experiments, a) Side view of a construct with an outer layer of 10% (w/v) GelMa, 0.5% (w/v) alginate and $6 \times 10^6$ HUVEC cells $mL^{-1}$. b) Transversal view of the previous construct, c) Effect pre-crosslinked cell concentration on layer's width and number of encapsulated cells in the layer.

Fabrication of hydrogel layers enclosing the alginate mandrel were fabricated based on a GelMa solution with homogenously distributed cells. After crosslinking, the alginate mandrel is removed or dissolved forming the lumen of the cellularized vessel graft (see FIG. 8(a)). These results evidence the capability of the dipping technology to allow the fabrication of a complete layer of encapsulated cells that are evenly distributed along the axial axis The effect of cell concentration on the width of the cellularized layer and the number of encapsulated cells per $mm^2$ was measured (FIG. 8(c)). As expected, no significant difference in width of the layers was found at different cell concentrations. The front and middle section are very similar when cells are seeded at 4 and $6\times10^5$ cells $mL^1$ and it is slightly wider at $8\times10^5$ cells $mL^1$, but under this last condition the values of layer's width has a broader distributions.

Encapsulated cells number per $mm^2$ was determined after dividing the total cell number in a determined area by the corresponding cylindrical section. Even though the concentration of seeded cells showed no significant effect on the amount of final encapsulated cells, it is possible to observe a tendency for a higher number of encapsulated cells when the concentration of cells mixed in the pre-crosslinked solution increases. Additionally, cells seeded at $6\times10^5$ cells mL$^{-1}$ appear to have a more even distribution of cells across its axial axis, as evidences by the similar number of encapsulated cells at the front and mid sections.

Cell Viability.

One important challenge of bio-fabrication technique that includes the embedding of live cells in the process is the cell viability post fabrication. The mechanical stress, UV treatment required for polymerization, cell handlings in non-physiological conditions are many insults that can either alter the cell function or result in their death. In order to challenge the fabrication method, vessel grafts compose of one individual cell-laden layer were fabricated using and standard protocol of dipping (10% (w/v) GelMa, 0.5% (w/v) alginate, 0.5% (w/v) PI, $6\times10^6$ cells/ml and emersion speed of 6.9 mm/s and a mandrel rotation of 42 rpm) and photo-crosslinking with 3 different level of UV irradiation at 365 nm wavelength (121, 261, 323 mW/cm$^2$). Considering the circumferential diameter of the light beam and the upward-speed, total UV exposure time is 4.36 s. The cylindrical cellularized layer with 150 um width was incubated in culture media, and proliferation and viability testing performed at day 1, 2, 4 and 7 (see FIG. 9). The cell proliferation and viability were then evaluated by measuring the metabolism of tetrazolium salt WST-1 to formazan and LIVE/DEAD staining respectively. Results showed important robustness of the system concerning maintenance of cell proliferation and viability at the different irradiation levels.

Figure 9:
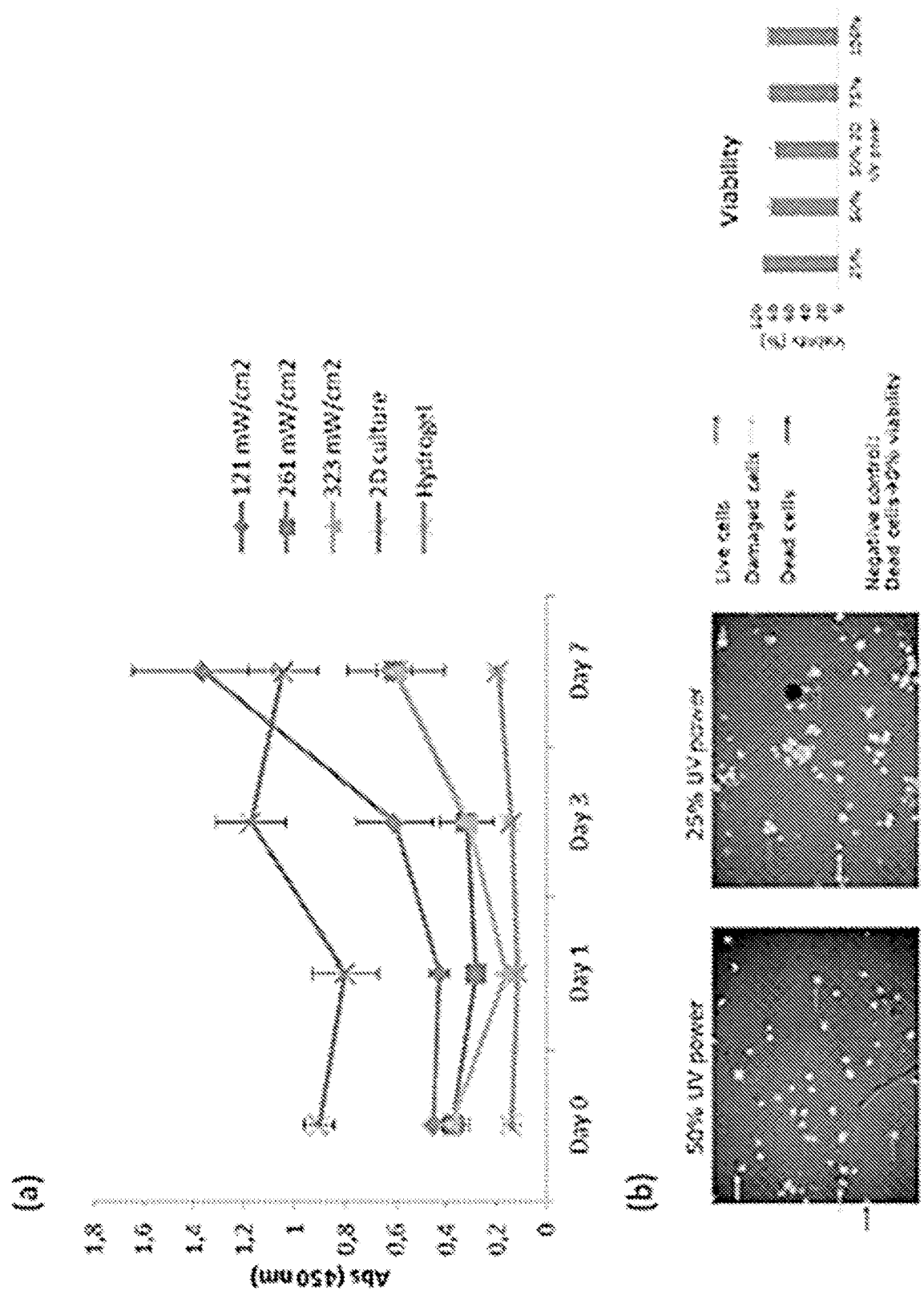
FIG. 9. Proliferation and viability assessment of encapsulated cells, a) Encapsulated HUVEC cells in a 150 ⌐T width cylindrical construct were subjected to WST-1 cell proliferation colorimetric assay (K302, Biovision, USA), b) Additionally, LIVE/DEAD assay was performed in order quantify cell viability after fabrication (R37601, Thermo Fisher Scientifics, USA). In both experiments, 3 different UV irradiation conditions were tested (121, 261, 323 mW/cm$^2$) and the measurement performed at day 0, 1, 3 and 7.

Comparing the results of time-dependent proliferation using different UV irradiation and the same amount of PI, there is no significant difference. However, when comparisons of time-dependent proliferation are performed amongst the different PI % using the same UV irradiation level, significant differences were observed. This is in line with previous results establishing a broader deleterious effect of PI compared to the effect of UV alone. Likewise, results of cell viability in FIG. 9 showed important robustness of the system when using different irradiation levels with 0.5% PI, observing similar results on day 0, 1 and 3. However, on day 7, viability at irradiation of 121 mW/cm$^2$ was 70%, whereas the higher irradiation level showed decreased to 60% of viable cells, indicating a later cellular dead possibly due to the combined effect of PI plus higher irradiation.

Biomaterial Micro-Deposition

In the typical structural configuration of natural SDBV, intercalated thin elastin layers and fiber across the vessel wall are a major component responsible for the mechanical properties of vessels. There is a sub-endothelial internal elastic membrane, separating endothelial layer from the smooth muscles cells (tunica media), which contains as well interpenetrated but few elastin fibers. Between smooth muscle cells and the adventitia layer a second elastin membrane constitute a second mechanically important element of vascular tissues. Fabrication of tissue engineered SDBV capable of mimicking the natural configuration of important super thin layers, such as endothelial layer and elastin membranes, would ideally requires a high precision method for micro-deposition of thin biomaterial layers and cells. In order to explore the feasibility of controlling micro-deposition of biomaterial with our automated system, low viscous 10% (w/v) GelMa solution was used to performed mandrel dipping and UV photo-crosslinking rounds. In FIG. 9(a) a cylindrical structure composed of 5 layers, 3 gelatin layers supplemented with I mg/ml BSA-FITC and 2 intercalated layers without BSA-FITC, was fabricated. Each layer fabrication comprises 25 rounds of mandrel dipping and photo-crosslinking, and the calculated size for every deposited micro-layer in a single round was about 1 um width, which gives a total of 25 um width per layer.

Figure 10:
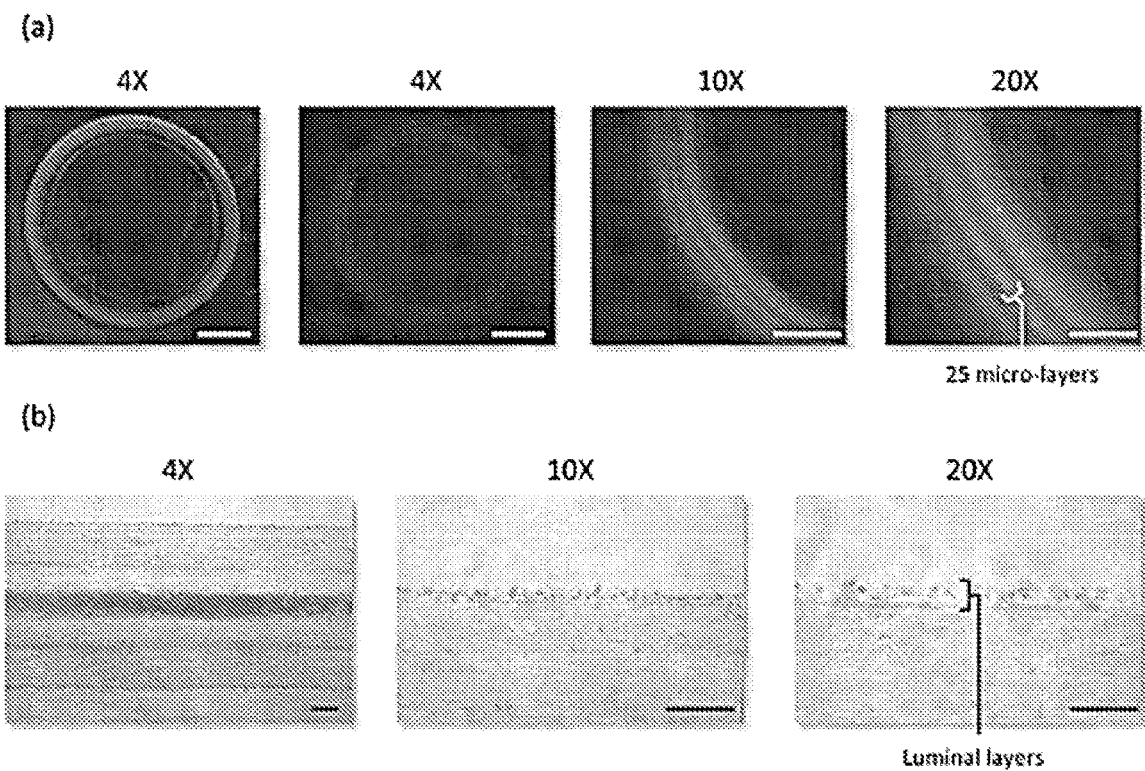
FIG. 10. Micro-deposition of GelMa and cellularized layers, a) Cylindrical construct of 3 Layers of 10% (w/v) GelMa and 1 mg/ml BSA-FITC (A9771, Sigma, USA) and 2 intercalated layers of 10% (w/v) GelMa solution. Each layer is fabricated through the deposition of 25 micro-layers (25 rounds of dipping/crosslinking). b) micro-fabrication of a thin HUVEC-derived cellularized layer. After testing different protocols, the system was able to obtain a stable cellularized layer of 20-30 um width. Scale bars: 4× (400 um), 10× (200 um), 20× (100 um).

In a similar way, the system was subjected to different testing in order to get a consistent and very thin layer with encapsulated HUVECs cell, with the goal of forming and hydrodynamically stable endothelial layer. Using a programed protocol of 3 rounds of dipping/photo-crosslinking using a solution of 10% (w/v) GelMa, 0.5% (w/v) PI, 0.1% (w/v) alginate and $5\times10^5$ cells/ml, where UV irradiation was 261 mW/cm$^2$, upward-speed 6.9 mm/s and a rotational speed of the mandrel 42 rpm. The dipping machine was able to obtain a highly cellularized layer of approximately 20-30 um width (see FIG. 10(b)). A future perspective is that this HUVECs-laden layer would constitute a confluent monolayer after appropriated hydrodynamic stimulating during in vitro or in vivo maturation.

Control of Graft Microstructural Alignment

Cells alignments have a fundamental role in the functionality of tissues, and blood vessels are not an exception. Circumferential aligning of smooth muscle cells confers the ability of contraction/dilation and blood pressure control to the arteries, whereas the alignment of endothelial cells in the direction of the flow reduces the presence of cell adhesion molecules, hence decrease platelets and leukocytes attachment phenomenon. It has been already well described how micro- and nano-structural alignment of biomaterials induces cell alignment and functionality.

Figure 11:
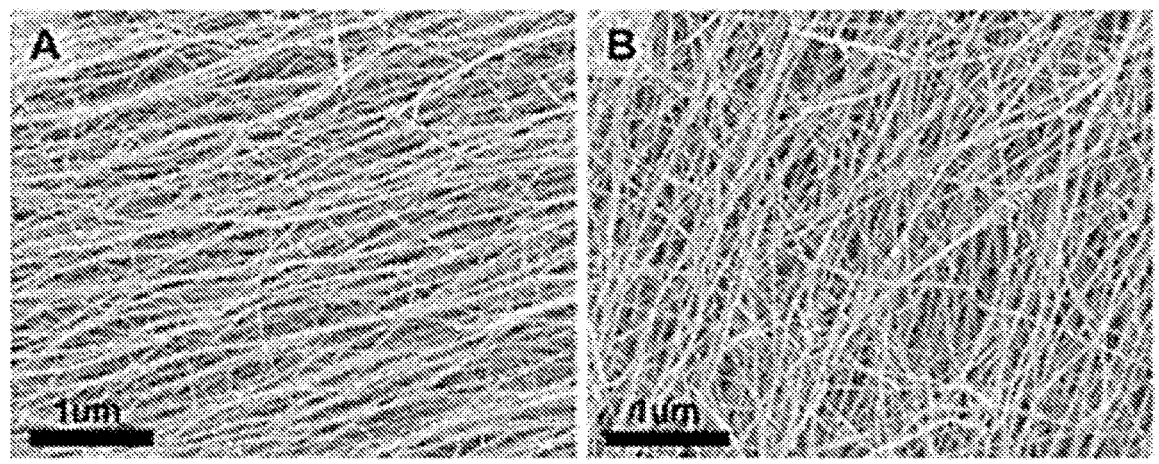
FIG. 11. Micro-structural alignment of GelMa hydrogel. a) Scanning electron microscopy of cylindrical hydrogel structures fabricated at a rotational speed of 14, 98 and 210 rpm respectively. b) Orientation of micro and nano fibers of constructs fabricated at different rotational speeds. Samples were prepared using ethanol dehydratation, critical point drying and coating of 8-nm thick Au/Pd.

In the present automatized device, Motor Z was originally assembled to allow homogenous crosslinking induced from a lateral fixed UV source; however, we envisioned the possibility of controlling matrix alignment of crosslinked hydrogels by modifying the rotational speed of motor Z. We tested two biomaterial conditions, one comprised a 10% (w/v) GelMa concentration and 0.1% (w/v) alginate, and the second was based on 10% (w/v) GelMa only. Graft fabrication was performed after 50 rounds of dipping and polymerization using three different rotational speeds (14, 98 y 210 rpm). Correlation between rotational speed and matrix alignment is observed in FIG. 11, showing a circumferential alignment at higher speed, while at lower speed, structural alignment approaches to lining orientation to the upward mandrel movement (motor Y). Notably, by controlling rotational speed, the system could generate circumferential alignment at higher speed, constituting possibly better functional smooth muscle tissue when seeded with smooth muscle cells. This has been previously described with other system that generates circumferential alignment. Similarly, very low rotational speed recreates linear microstructural alignments. During emersion of the mandrel from the dipping solution, the pre-crosslinked biomaterial still adhered to the mandrel tends to flow down due to gravitational effects. This orients linearly to the graft length the hydrogel microstructure before crosslinking, possibly allowing alignment of endothelial cells to a less thrombogenic luminal surface configuration, as previously explained.

Vessel Structure Fabrication

Figure 12:
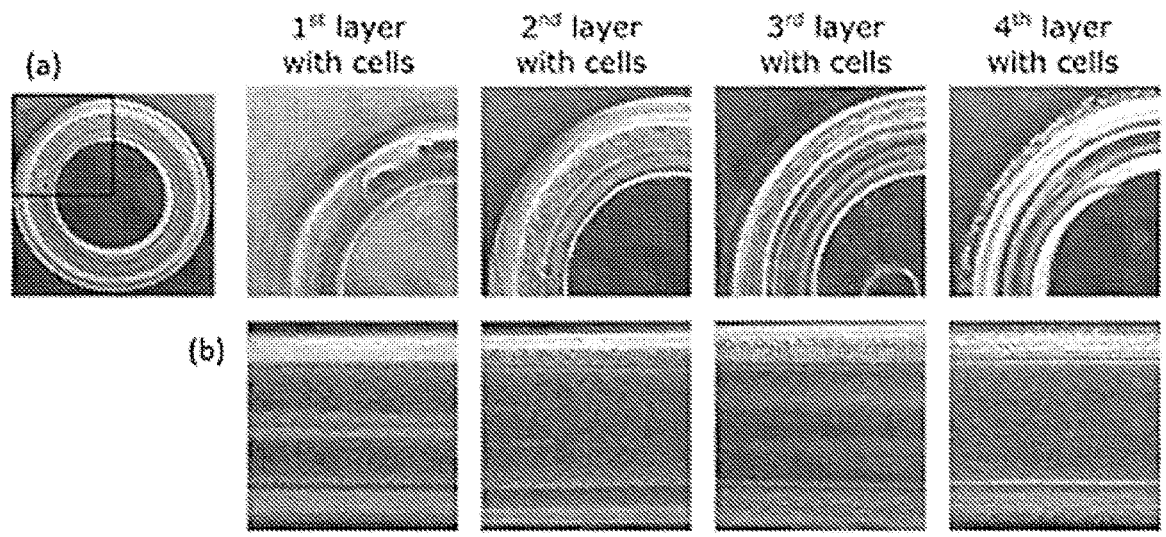
FIG. 12. Concentric positioning of cellularized layers. 4 different 4 layers constructs harboring a single cellularized layer at different concentric positions were fabricated to show precise location of cell content in a vessel graft fabrication process. Location order goes from the inner layers to outer layers. Figure shows a) transversal and b) sagittal microscopy view of the fabricated grafts.

Even though the fabrication system proposed in this work follow relatively simple procedures, complex structures with precise positioning of layers can be constructed with this automatized method. The precision level of encapsulated cells positioning was evaluated in structures built over an alginate mandrel structure, and are consisted of four hydrogel layers of 10% (w/v) GelMa with 0.2% (w/v) alginate, where only 1 of these layers contained encapsulated cells (FIG. 12(a), (b)). The coating layer with encapsulated cells was positioned first in the luminal area followed by the subsequent non-cellularized layers. In the consecutive pictures the only cell-laden layer is positioned second, third and fourth respectively. These results reflect a well-controlled positioning of cellularized layers that can be achieved with the proposed technique and device. Finally, it is important to add that the mechanical strength of the materials and the tight interactions between layer interfaces due to methacrylic group crosslinking allowed the maintenance of the structure, geometry and integrity even after removal of the alginate mandrel.

A second structure, with higher complexity, was fabricated to prove the versatility in making more complex and multi-material vessel grafts. The constructed graft was obtained after coating an alginate mandrel with encapsulated HUVEC cells in 10% (w/v) GelMa, 0.2% (w/v) alginate and supplemented with BSA-FITC (I mg/ml) for fluorescence visualization, followed by 25 micro-layers derived from dipping/crosslinking in 10% (w/v) GelMa solution, 1 layer of 10% (w/v) GelMa, 0.2% (w/v) alginate and BSA-FITC, 25 micro-layers of 10% (w/v) GelMa, 1 layer of 10% (w/v) GelMa with 0.2% (w/v) alginate and BSA-FITC, and an outer layer composed of 25 micro-layers of 10% (w/v) GelMa. In FIG. 13(a), it is possible to distinguish all 6 layers of the construct, and by examining FITC's fluorescence of intercalated layers deposited with this technology (see FIG. 13(b)), we can deduced that layer did not mix or were not ripped during the production process. Additionally, FIG. 13(c) shows a close-up of the first layer were the encapsulated cells at the luminal region can be appreciated more clearly. In this last experiment, prove the feasibility of using different materials and the control of deposition and microdeposition of several layers assembled together, leading to the fabrication of a structurally similar blood vessel configuration (tunica intima, media and externa intercalated with elastin layers).

Multilayer cylindrical structures with bovine methacrylated gelatine (GelMa) layers, encapsulated cells and polycaprolactone (PCL) meshes were constructed using a combination of Dipping-Spinning technology and SBS.

Figure 14:
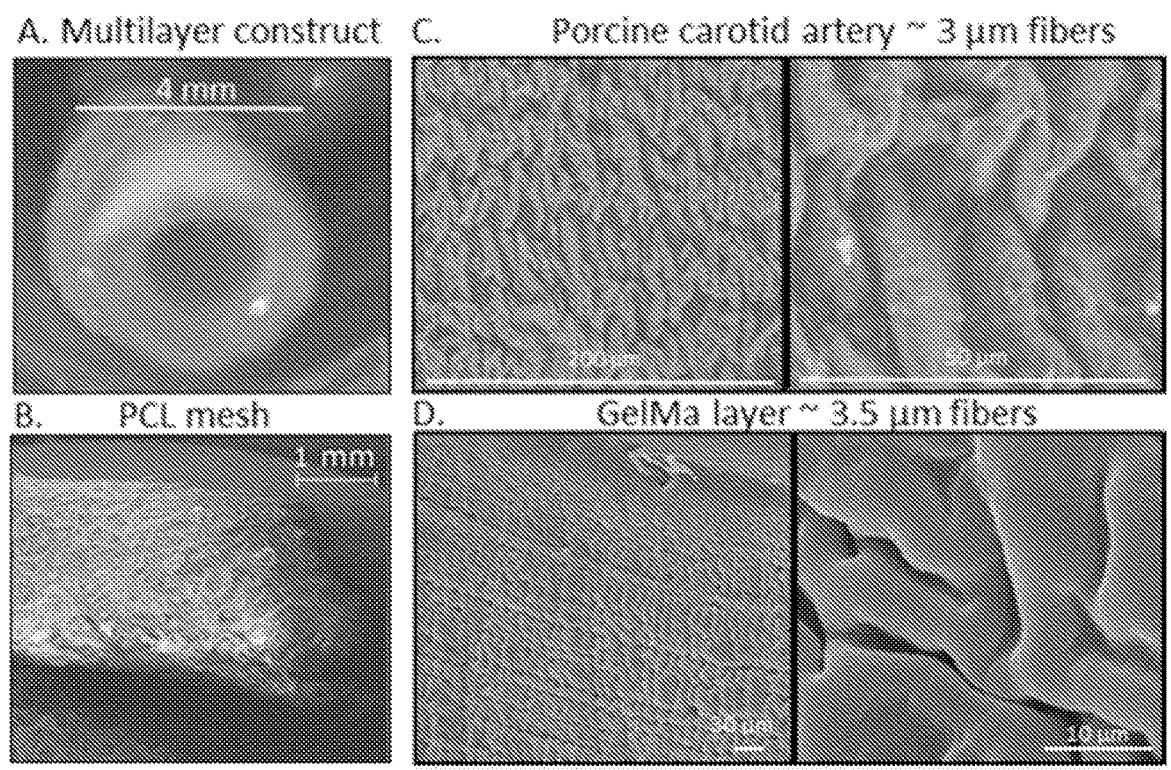
FIG. 14: A. Complex multilayer construct with layers of alginate and PCL meshes. B. SEM image of a cylindrical structure covered with PCL spun fibres (40×) C. SEM micrograph of a decellularized porcine vessel D. SEM micrograph depicting the alignment of GelMa layers micro-deposited using the Dipping-Spinning technology.
Figure 15:
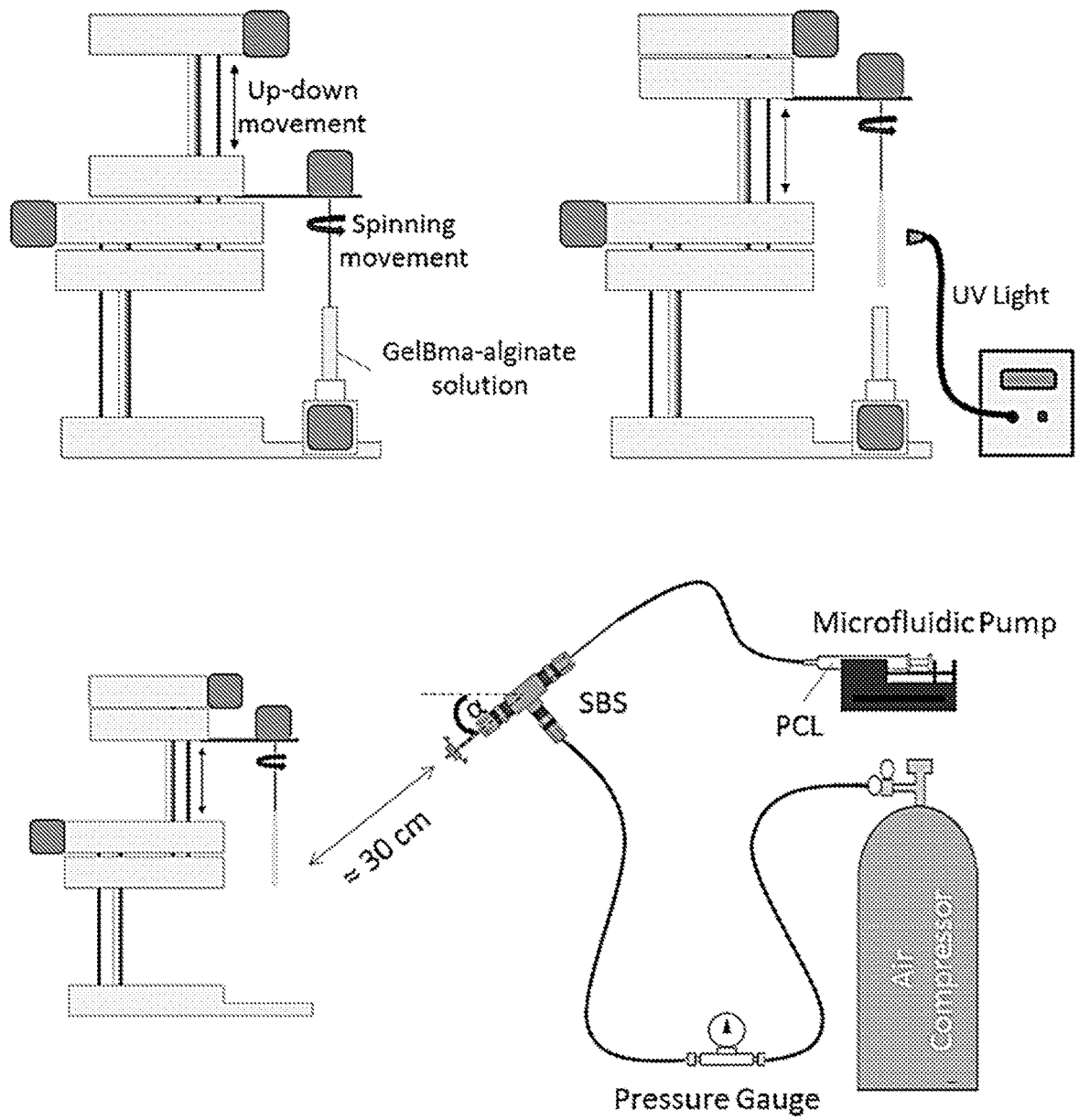
FIG. 15. Fabrication of GelBMa reinforced with PCL fibers vascular grafts. Tubular scaffolds were fabricated combining the SBS and dipping-spinning technique. A) Fabrication of GelBMa-alginate sub-layers through a dipping in GelBMa-alginate solution and spinning for the exposure to UV light. B) Fabrication of PCL fibers sub-layers through the spun of fibers with the SBS technique into a spinning rod.
Figure 16:
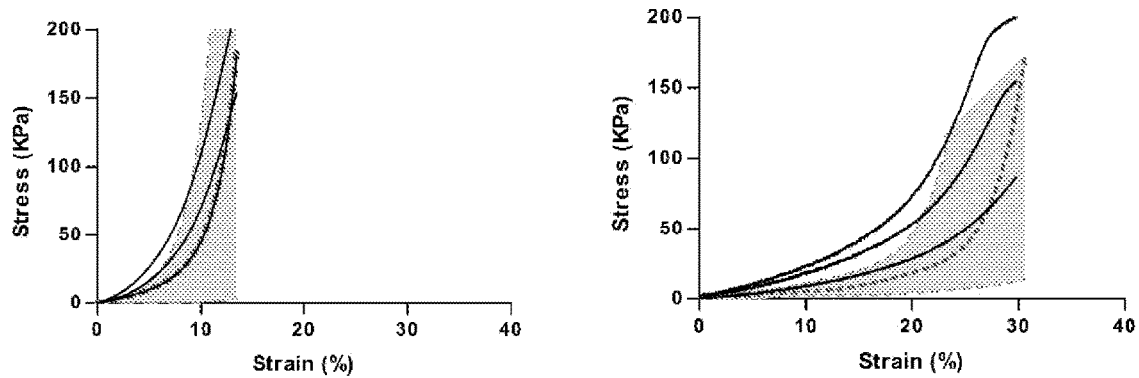
FIG. 16. Stress-strain curves of middle layer of GelBMa reinforced with PCL fibers in 21° vascular graft (line) and human coronary artery media layer model response (grey dotted line) with the range (light grey) in a) longitudinal and b) circumferential directions.
Figure 17:
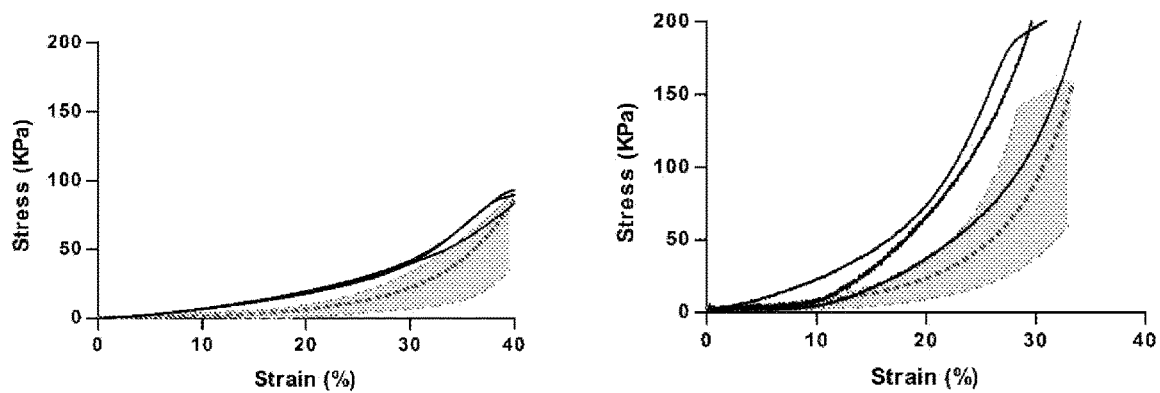
FIG. 17. Stress-strain curves of outer layer of GelBMa reinforced with PCL fibers in 67° vascular graft (line) and human coronary artery media layer model response (grey dotted line) with the range (light grey) in a) longitudinal and b) circumferential directions.
Figure 18:
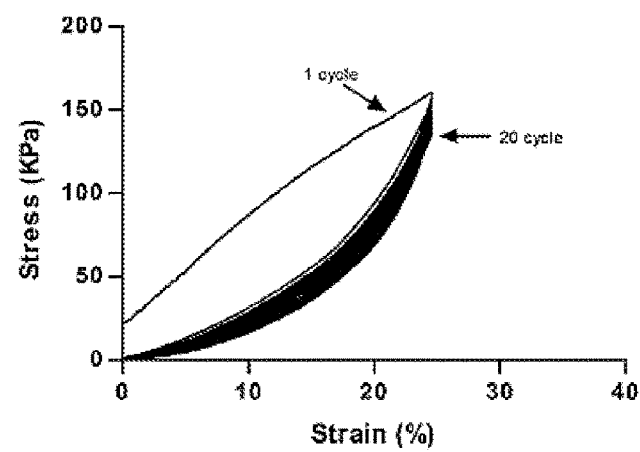
FIG. 18. Cyclic tensile testing of GelBMa reinforced with PCL fibers vascular graft in circumferential directions.

In depth analyses of these layers using SEM imaging show that they present a microstructure that mimics the one observed in the matrix of natural vessels (FIGS. 14 C and D). Finally, mechanical findings indicate that PCL meshes enhance the structures' tensile strength towards achieving desired mechanical properties.

The coating with PLC fibres was performed according to the following conditions:
PCL, average molecular weight 65000, 15% w/v in acetone/chloroform 20%/80%; injection 200 uL/min, air pressure 40 psi; and
PCL, average molecular weight 80000, 7% w/v in acetone/chloroform 20%/80%; injection 120 uL/min, air pressure 60 psi.

The construct can be manufactured with different combinations of gelatin layers (with or without cells) and PCL layers, it all depends on the requirements of the design.

Example 2

Robotic Device (as Described in Example 1)
Preparation of GeIBMa-Alginate Solution.
Methacrylated bovine gelatin, or GeIBMa, was synthesized by mixing bovine gelatin (Bloom 220, Rousselot, Netherlands) and methacrylic anhydride to a final concentration of 8% (v/v) as previously dissolved in PBS 1× (pH 7.4) at 60° C. for 3 hrs. as previously described (Nichol et al. 2010; Van Den Bulcke et al. 2000). Three stock solutions were prepared. GeIBMa stock solution was prepared by dissolving freeze dried GeIBMa in PBS 1× at 40° C. at a concentration of 20% (w/v). Alginate stock solution was prepared by dissolving medium viscosity sodium alginate (A2033, Sigma, USA) in PBS 1× at 60° C. at a concentration of 2% (w/v). The PI stock solution was prepared by dissolving 2-Hydroxy-4'-(2-hydroxyethoxy)-2-methylpropiophenone (410896, Sigma, USA) in PBS 1× at 85° C. until fully dissolved. The GeIBMa-alginate solution was prepared by mixing the three stock solutions to a final concentration on 10% (w/v) of GeIBMa, 0.5% (w/v) of alginate and 0.2% (w/v) of PI. For the $CaCl_2$ solution, $CaCl_2$ was dissolved in $ddH_2O$ at a concentration of 5% (w/v).

Deposition of PCL Sub-Layers.
PCL layers were fabricated from a PCL (440744, Sigma-Aldrich, USA) with a combination of custum-made solution blow spinning (SBS) and robot device. PCL was dissolved at 7% (w/v) in a chloroform/acetone mixture ratio 80/20 (v/v). Consisted of compressor (Huracan 1520, Indura, Chile) as a source of compressed air, equipped with a pressure regulator to control the pressure in 40 psi, a 10 mL hypodermic syringe, a syringe pump (NE-4002X, New Era Pump Systems, Inc. NY, USA) to control the injection rate of the PCL solution at 120 µL/min, a spraying apparatus that consisted of concentric nozzles, and the plastic rod of the robot device moving down and up at 138 mm/s upward-speed for the fiber deposition. During all the down-up movement a constant spinning movement was performed. The complete spin-down-up movement takes 30 sec. The distance between the SBS nozzle and the place of fiber deposition in the rod was 30 cm.

For each layer fabrication the SBS nozzle was orientated in a certain degree in order to spun and deposit the fibers in a certain direction. The fibers were deposited while the rod was moved down and up for with a permanent spin that consist in 1 s at +165 CP and 0.5 s at −165. In order to deposit the fibers in the opposite degree the robot device orientation was switched backwards and the spinning movement was changed to 1 s at −165 CP and 0.5 s at +165 CP.

Deposition of GeIBMa-Alginate Sub-Layers.
GelBma-alginate layers were generated with a custom-made robot device. Each layer is fabricated through several dippings of a rod previously covered with a PCL layer into the GelBma-alginate solution. The solution was kept in a water bath at 30° C. to avoid spontaneous gelation at room temperature. Crosslinking was achieved by exposing the gelatin solution to UV light at 365 nm wavelength (261 mW/cm$^2$) (OmniCure S2000, Excelitas Technologies, USA) from a distance of 2 cm while the coated mandrel was rotating and emerging from the pre-crosslinked solutions at 165 cP and 138 mm/s upward-speed.

Fabrication of Middle and Outer GeIBMa Reinforced with PCL Fibers Layers
Middle and outer layer were fabricated intercalating GeIBMa-alginate and PCL fibers sublayers. The middle layer consisted in 4 intercalated sublayers of PCL fibers and GeIBMa. For the middle PCL sub-layer the SBS nozzle was oriented at −21°. First a complete spin-down-up movement was performed with the robot device looking to the front in order to deposit the fibers at +21°. Then a complete spin-down-up movement was performed with the robot device looking backwards in order to deposit the fibers at −21°. For the GeIBMa sublayer the rod covered with fibers was drop into the GeIBMa-alginate solution and kept there for 30 s in order to let the solution permeate the PCL fiber sub-layer.

Middle GeIBMa-alginate sublayer consisting in 2 dippings was deposited covering the PCL fiber layer. The outer layer consisted in 5 intercalated sub-layers of PCL fibers and GeIBMa. The same general methodology with some change of parameters was used for the outer layer. For the outer PCL sub-layer the SBS nozzle was oriented at −67° and the outer GeIBMa layer consisted in 3 dippings.

In order to image the PCL fiber orientation middle and middle-outer layer with and without the deposition of the last GeIBMa sub-layer were fabricated and imaged with Scanning Electron Microscopy (SEM, LEO 1420 VP). The fiber diameter and layer thickness was measured with the ImageJ software (National Institutes of Health, USA). The outer layer thickness was measured as the difference between the thickness of middle-outer layer and middle layer.

Fabrication of GeIBMa Reinforced with PCL Fibers Vascular Grafts

GeIBMa reinforced with PCL fibers vascular grafts consisted in three layers: inner, middle and outer. A thin mandrel of alginate was deposited in order to have a smooth and easy separation of the vascular graft from the plastic rod. The alginate mandrel was fabricated through 2 dipping into the alginate stock solution followed by a 15 s dipping into the $CaCl_2$ solution for polymerization and finally immersed 3 times in PBS for 1 min for cleansing. For the inner layer a GeIBMa sub-layer consisting in 9 dippings was fabricated covering the alginate mandrel. Over the inner layer the middle GeIBMa reinforced with PCL layer was manufactured. Subsequently, the outer layer was fabricated around the alginate-inner layer-middle layer construct. Finally, the plastic rod and alginate mandrel were removed mechanically.

The structure of GeIBMa reinforced with PCL fibers vascular grafts was acquired with a Micro CT.

Tensile Test

Uniaxial tensile test of GeIBMa reinforced with PCL fibers middle layer and outer layer were performed in a Texture analyzer. The axial force was measured with a 5 N load cell. The samples were cut in longitudinal and circumferential directions and maintained at 37° in PBS 1× (pH 7.4). For each layer 3 samples were tested. Sample thickness and width was measured on each sample. Sample length was obtained by initial position of the texture analyzer. Before the testing was done, five loading and unloading cycles at a constant rate of 10 mm/s was achieved as preconditioning of the samples. The loading cycles were until a strain of 13% for the longitudinal test of the outer layer, 30% for the circumferential test of the outer layer and longitudinal test of the middle layer and 35% the longitudinal test of the middle layer. The axial testing of circumferential and longitudinal samples was performed at a constant rate of 10 mm/s.

Uniaxial tensile test of GeIBMa reinforced with PCL fibers vascular grafts were performed in a universal testing machine. The axial force was measured with a 5 N load cell. The samples were cut in longitudinal and circumferential directions. The samples were maintained and tested while being permanently submerged in physiological serum 1× (PBS) at a temperature of 37°±0.5° C. For each vascular graft 6 samples were tested. Sample thickness, width and length were measured with an optical extensometer with 0.001 mm of precision. Before the testing was done, five loading and unloading cycles until a strain of 30% at a constant rate of 10 mm/s was achieved as preconditioning of the samples. The axial testing of circumferential and longitudinal samples was performed at a constant rate of 1 mm/s.

In order to test the resistance to circumferential deformation, GeIBMa reinforced with PCL fibers vascular grafts were cut in circumferential direction and were subjected to 20 repeating loading-unloading cycles of circumferential stress until a strain of 30% at a constant at a constant rate of 10 mm/s.

The stress and strain curves for all tests were derived from axial load and clamps displacement recorded during the test. The stress was computed as F/A, where the F is the axial load with a precision of 0.01N and A is the initial cross-sectional area. The strain was computed as $100*L/L_0$, with L and $L_0$ as the current length and initial sample length, respectively.

Pressurization Test

This test intends to study the response of GeIBMa reinforced with PCL fibers vascular grafts under in vivo loading and pressure conditions. This test was performed in a custom set up placed inon a universal testing machine and designed for this test. It consisted of a plastic transparent chamber filled with PBS 1× at of 37°±0.5° C. The application of internal pressure was with an auxiliary line of PBS at 37° C. The pressure was measured at the entrance of the chamber with a pressure transducer and the sample diameter was measured with an optical extensometer. Five samples were tested. Before the testing was done, five loading and unloading cycles until a strain of 30% at a constant rate of 10 mm/s was achieved as preconditioning of the samples. The vascular grafts were subjected to three different constant axial strains of 10%, 20% and 25%. To preconditioning the sample in the circumferential direction, 5 cycles of 0-200 mmHg of pressure were performed.

The compliance of the vascular grafts (% C) was computed from the experimental data at three pressure ranges (50-90, 80-120, 110-150 mmHg), according to standard ISO 7198 (ANSI/AAMI/2010)

$$\% C = \frac{R_{P_2} - R_{P_1}}{P_2 - P_1} * 10^4$$

Where $P_1$ and $P_2$ is the lower and higher pressure valve in mmHg and the $R_{P1}$ and $R_{P2}$ are the external radius in those pressures respectively.

Viability and Proliferation Tests

Human Umbilical Cord Cells (HUVEC) was mixed in the GeIBMa-alginate solution at a concentration of 10 milllion $ml^{-1}$. Vascular grafts were fabricated as mentioned before using the GeIBMa-alginate with HUVEC solution in order to encapsulate the cells in the GeIBMa-alginate sublayers.

Cell proliferation test were performed in 5 mm of length vascular grafts using the WST-1 Cell Proliferation Colorimetric Assay Kit (K302, Biovision, USA). Briefly, this assay quantifies the metabolic cleavage of WST-1 to generate formazan by cellular mitochondrial dehydrogenases. The samples previously washed in PBS were immersed in 200 μL of culture medium and 20 μL of WST reagent for 2 hrs and 30 min. The proliferation was measured for 1 day and 7 days after the vascular grafts fabrication was done.

For the cell viability test, 5 mm of length vascular grafts were washed for 30 min in PBS at 37° C. Subsequently, the vascular grafts were incubated in LIVE/DEAD® Cell Imaging Kit (488/570) (R37601, Thermo Fisher Scientifics, USA) reagent for 20 min and washed for 30 min in PBS at 37° C. again. Using a criostate, 20 μm transversal cuts were made to the vascular grafts. The samples were visualized using a light microscope to observe living and dead cells.

Photographs of three parts of each sample were taken with a digital camera. Images were processed and cell counting was performed with the ImageJ software (National Institutes of Health, USA). Cell viability in vascular grafts (%) was calculated as dead/total cell ratio.

Results

Middle and outer layers of GeIBMa reinforced with PCL fibers vascular grafts showed an anisotropic and nonlinear mechanical response resembling the media and adventitia layers of human coronary arteries. The outer layer showed a stiffer behavior in the longitudinal direction, whereas the middle layer is stiffer at the circumferential direction. An opposite response is observed between the middle and outer layer in each direction. At the longitudinal direction the middle layer is more compliant; however, at the circumferential direction middle layer tends to be slightly stiffer than the outer layer. The stiffness and the deformation profile (shape of the stress-strain curve) of each layer of human coronary arteries could be tailored by adjusting the quantity (time of SBS deposition) and orientation of PCL fibers and the thickness of the GeIBMa layer (quantity of dipping).

When inner, middle and outer layers are tested together in the vascular graft the nonlinear response and clear anisotropy is maintained. In addition, a similar behavior to human coronary arteries was achieved in both directions, being stiffer the longitudinal direction.

To verify whether the GeIBMa reinforced properties change between the fabrication and the final application, 20 repeating loading-unloading cycles of circumferential stress were performed to a vascular graft strip. A linear response is shown in the first cycle. However, after the first cycle a non-linear and anisotropic behavior is observed and converges to a certain stress-strain curve shape with smaller hysteresis.

Figure 4:
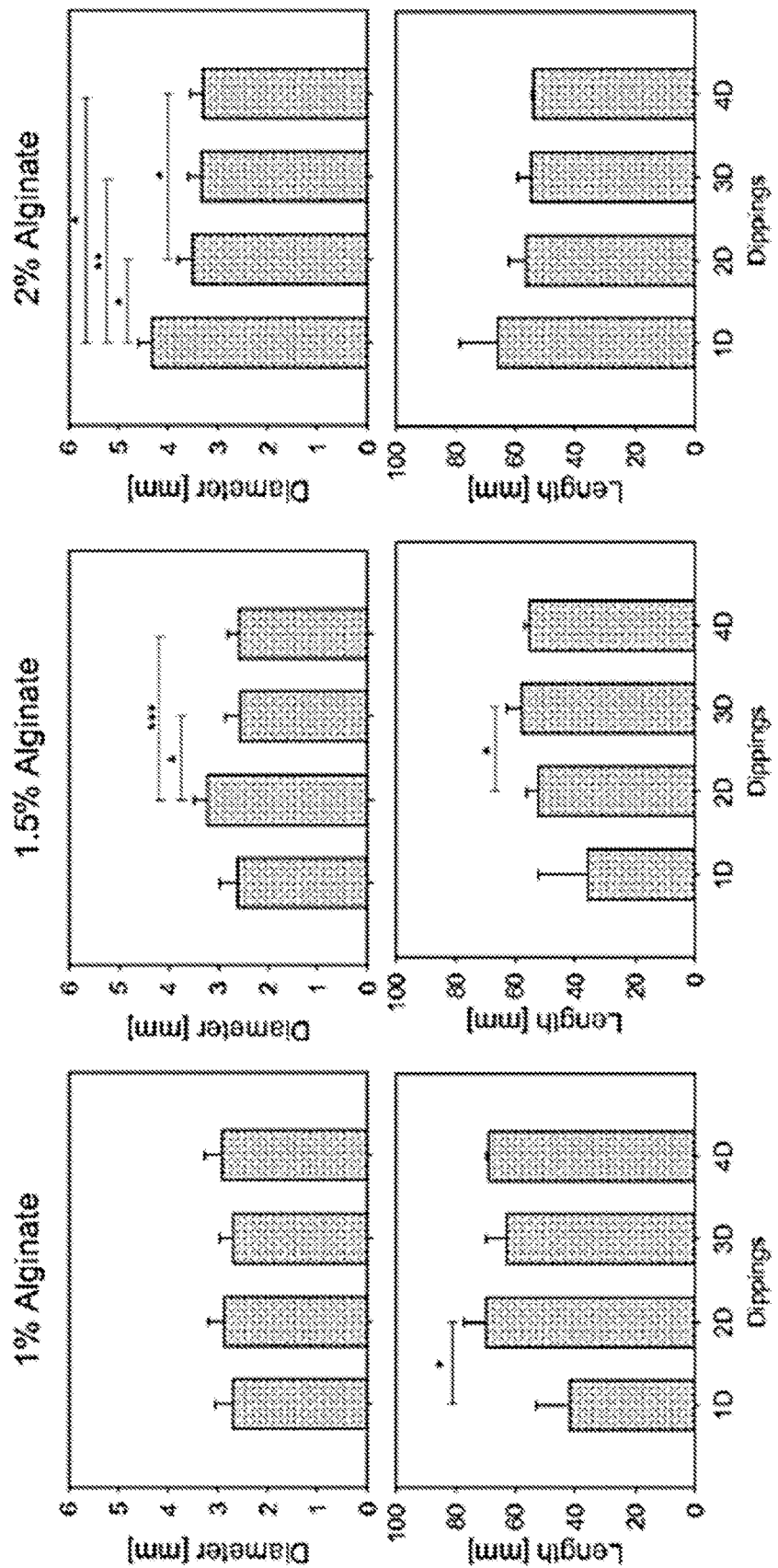
FIG. 4: Lumen structures' average diameter between front and mid, and dimensional length of obtained constructs. The structures were constructed with 2 rounds of alginate dipping with 138 mm/s as upward-speed; the first was done with 2 dippings in 2% alginate and the second with 1, 2, 3 or 4 dips in a 1, 1.5 or 2% (w/v) alginate solution. * $p<0.05$;  $p<0.005$; * $p<0.001$.

The vascular grafts were tested at different values of axial prestretch and compared with human coronary artery response. A J-shape response was obtained at the diameter-pressure curves and was not altered by the plastic deformation suffered at higher axial elongation. When compared with human coronary arteries, vascular grafts showed a more compliant response. In the approximated in situ length, vascular grafts showed a greater increase in external diameter with pressure compared with human CA (FIG. 19). At 20% and 25% axial elongation similar values of nominal diameter change to human CA are observed (FIG. 4.*a* and FIG. 4.*b*).

The compliance values for vascular grafts with 10 and 20% of prestretch have no statistical difference with the human coronary arteries at all pressures ranges. These results highlight the statistically similar compliant response that vascular grafts have at the close physiologic range of pressure (80-120 mmHg). Nevertheless, at higher values of axial elongation statistic difference between compliance of human CA and vascular grafts were obtained in any range of pressures (Table 3, see FIG. 19).

CONCLUSION

The present invention provides a method that can be easily automatized based on a conceptually simple fabrication strategy, such as dipping and polymerization, and can reach impressive control of lumen diameter, deposition and micro-deposition of multilayers in a rapid and versatile manner, allowing for complexity and scalable fabrication of multiyear hollow tubes which can mimic natural tissues such as vascular grafts, urethral grafts and prostate grafts.

According to the present invention, the fabrication of complex multilayer cylinders can be carried out combining coats designed for biological and mechanical purposes. The precision achieved by the system reduces variability and increase significance of results.

The automatized dipping system is based on the control of four stepper motors using a programmable microprocessor. Two motors control the dipping process while a third motor the rotational movement of the graft during the process of fabrication, allowing a homogeneous polymerization or crosslinking from a fixed source of lateral UV light. This rotational movement was designed to control as well the micro-structural alignment of the deposited biomaterial by meaning of variations in the rotational speed. The fourth motor controls the rack placement in order to switch from one material to another, and its programed movements define the order of positioning of the different concentric layers across the vessel graft. A vascular construct composed of an endothelial layer, two additional cell-laden layers and two intercalated reinforcing layers, mimicking the arterial configuration (tunica intima, tunica media and tunica externa intercalated by two elastin layers), would require only 15 min programmed operation for complete fabrication.

Concerning the control of luminal diameter, an easy strategy would be the use of appropriated metal rods with different diameter for dipping and later mechanical pulling of the polymerized or crosslinked construct. However, the use of mandrels based on sacrificial material such as alginate, allows the delicate removal of vessel-like grafts keeping unscathed luminal cellularized thin layers, necessary to develop a mature endothelial layer. In this case, removal can be accomplished using calcium chelating agents for alginate depolymerisation or through calcium-driven compaction of the alginate mandrel and gentle graft displacement.

Fabrication of the luminal alginate mandrel based on the two variables, emersion speed (upward-speed) and alginate concentration or viscosity, describe a three-dimensional function, showing a positive correlation between viscosity or upward-speed and the final alginate mandrel diameter. Therefore, changes in viscosity and upward-speed parameters during fabrication can be utilized to control diameter sizes of vascular grafts using the automatized system, which will be the tools of control for later layer deposition too.

Our results indicate that up to 46 mm/s upward-speed, there is a direct proportion between the emersion speed and the obtained alginate mandrel diameter when using alginate concentration above 2.5% (w/v). However, using 2% (w/v) alginate solution at 138 mm/s upward-speed, the diameter variation along different section of the resultant alginate mandrel is minimal, becoming anyway the setting of choice to obtain usable longer and dimensionally homogeneous vascular grafts.

Dipping of a thin metal rod into an alginate solution proved to be a feasible way to customized luminal diameter of vascular grafts, whereby simply repetition of dipping rounds, it could permit larger vessel diameter above 6 mm, adding a major level of versatility to the fabrication system.

In order to limit the number of experiments, we explore the control of our system over the layer widths during fabrication by changing the viscosity value and keeping the upward-speed unperturbed. 10% GelMa solutions with different viscosity values were obtained after mixing with variable amounts of alginate. Positive correlation between viscosity and the layer thickness where only observed within a restricted range of alginate (0.075% to 0.15% (w/v)). Although it is possible to control the width of deposited biomaterial using this settings and modifying alginate concentration between 0.075% and 0.15% (w/v), wider range of alginate concentration for a better width control could be obtained if a different upward-speed is used, as it can be deduced from diameter results, where 4.6 mm/s upward-speed shows a slow increment in the diameter as the viscosity increases from 2% to 3% (w/v) alginate, whereas at 23 mm/s upward-speed the diameter increment is very high already from 2% to 2.5% alginate concentration.

In order to show versatility in terms of chosen biomaterial, beside alginate and gelatine, a third biomaterial was chosen based on its different mechanism of polymerization, different mechanical and biological nature, and the large number of described biomedical application, Chitosan can be polymerized using different methods such as coacervation/precipitation induced by alkaline solutions or ionic gelation. In this work, the system was adapted to perform ionic gelation using immersion in a polymerizing solution based on the polyanion, tripolyphosphate (TPP). In order to test feasibility of chitosan layer fabrication and width control, three different concentrations of chitosan were chosen to prove the possible dependency of viscosity on the layer thickness, and as well two different upwards-speeds at a fixed chitosan concentration to observe the possible effect of emersion speed on thickness.

Concerning upward-speed, significant differences were observed, while for the three viscous chitosan solution only a trend of positive correlation is observed. It is expected to reach significant positive correlation if the experimental settings are move to another point of the three-dimension function that explains the viscosity and upward-speed control in the level of deposited material by our system.

Natural blood vessels contain several intercalated fibres of mechanically reinforcing biomaterial. The present invention proved the flexibility of creating layers as thinner as 1 um, allowing micro-deposition of intercalated biomaterial for mechanical reinforcement. This provides an additional ability toward structural and mechanical closer mimicking of natural blood vessels.

One general challenging aspect in tissue engineering and tissue engineering (SDBV) using a cellularized scaffolds is the reduced capacity of cell re-population or invasion post-fabrication. The present invention overcomes this issue by mixing cells in the pre-polymerized solution previous to fabrication of layers. In this way the fabrication succeed in homogeneously distributing cells in the whole construct, furthermore localizing specific cells and biomaterials in concentric zone across the wall of vessel graft. The automatized methodology allows a high level of complexity in fabricating multilayer and cellularized blood vessel grafts.

Functionality of blood vessel grafts depends, in an important extend, on the integrity of confluentendothelial monolayer, especially to avoid thrombogenic phenomenon. In order to test the abilities of our system in generating a very thin and stable layer of encapsulated cells, given origin to a possible well-integrated endothelial layer after in vitro or in vivo maturation, we tested different conditions until getting a cellularized layer of HUVECs not wider than the size of 2 to 3 cells (20 um width).

Figure 13:
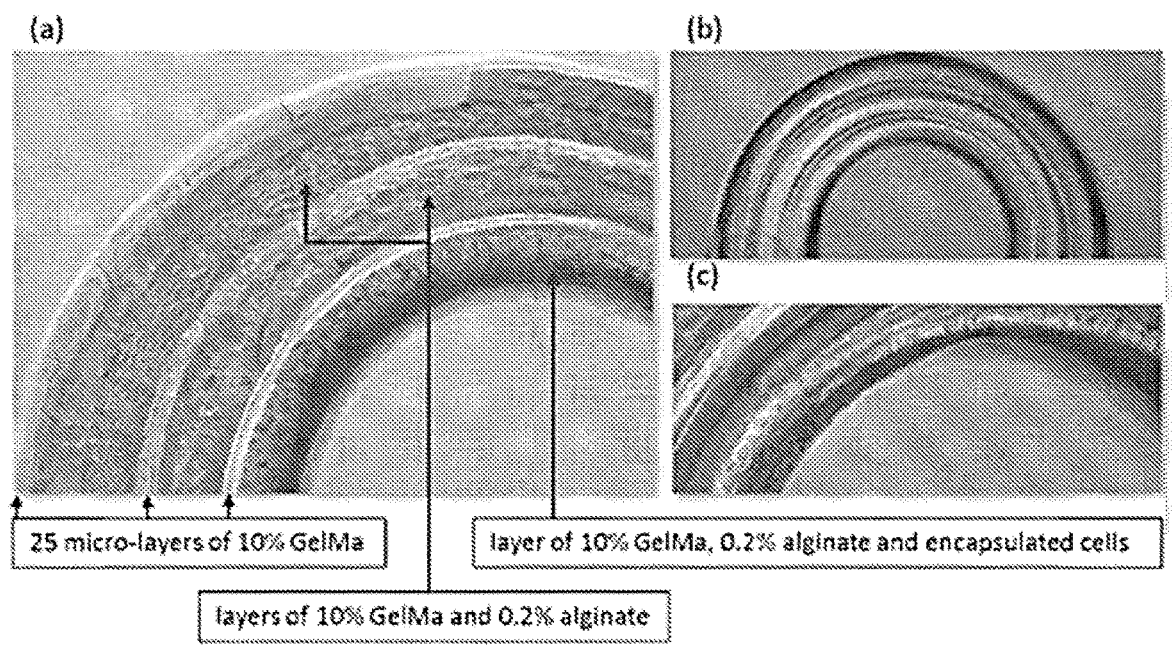
FIG. 13. Fabrication of complex vessel-like structures. A vascular graft with a similar layer configuration of natural blood vessel was fabricated. The complex construct consists of 1 layer of encapsulated cells in a 10% (w/v) GelMa, 3 intercalated sets of 25 micro-layers of 10% (w/v) GelMa and 2 layers of 10% (w/v) GelMa with 0.2% (w/v) alginate. All 10% (w/v) GelMa, 0.2% alginate layers were supplemented with 1 mg/ml of BSA-FITC for fluorescent visualization. a) Transversal view of the complex construct, b) fluorescent visualization of BSA-FITC supplemented layers and c) close-up of the layer with encapsulated cells.

A final experiment was performed to test the versatility of constructing complex multi-material and multi-layers vascular grafts. FIG. 13 shows a multilayer cylindrical construct comprising a cellularized internal layer, two gelatine/alginate based layer and three intercalated gelatine layer that serve as structural reinforcing elements. All layer to layer interfaces did not show any sign of detachment, most likely due to the presence of methacrylic groups in the gelatine that form covalent bonds during UV exposition, which forms not only in the layer, but as well at the interface between layers. This confers more structural integrity to the cylindrical construct. Other biomaterials such as chitosan, alginate, gellam gum, collagen, elastin, and cellulose can as well undergo methacrylation, therefore be included in a structural stable manner into multilayer constructs using this automatized system.

The invention claimed is:

1. A method for producing a multilayered construct comprising the steps of:
   (a) dipping a template into a pre-polymerized solution comprising gelatin, a photo-initiator and alginate or salts or derivatives thereof, wherein the gelatin is chemically functionalized to be reactive to polymerization or cross-linking in the presence of free radicals, and wherein the amount of gelatin in the pre-polymerized solution is in the range of 1-20% w/v;
   (b) exposing the pre-polymerized solution attached to the template to a wavelength of light, thereby stimulating the photo-initiator and causing the gelatin to polymerize or cross-link; and
   (c) depositing a polymer fiber layer on the template at an equal or opposite angle to a naturally occurring fiber angle, wherein the template is rotated and moved up and down while depositing the polymer fiber layer.

2. The method according to claim 1, wherein the gelatin of step (a) is functionalized using a chemical agent which provides methacryloyl, methacrylamide, acrylamide or acryloyl, or combinations thereof, functional groups at amino acid side chains of the gelatin.

3. The method according to claim 1, wherein the pre-polymerized solution further comprises viable cells, proteins, extracellular vesicles, genetic material, polynucleotides, drugs or polymeric particles, or combinations thereof.

4. The method according to claim 3, wherein the viable cells are selected from the group consisting of mesenchymal stem cells, endothelial cells, smooth muscle cells, fibroblasts, keratinocytes and chondrocytes.

5. The method according to claim 1, wherein the depositing of the polymer fiber layer is performed by means of solution blow spinning.

6. The method according to claim 1, wherein the polymer fiber layer is deposited in opposite angles or phases, or both, to form a mesh.

7. The method according to claim 1, wherein the naturally occurring fiber angle is 10 to 80° with respect to a template axis, and the polymer fiber layer is deposited at a−10 to −80° and 10 to 80° angle.

8. The method according to claim 1, wherein before steps (a) to (c): the template is dipped at least once in a solution comprising alginate or salts or derivatives thereof; and then dipped in a solution inducing polymerization of the alginate or salts or derivatives thereof.

9. A multilayered construct prepared according to claim 1.

10. An implantable prosthesis comprising the multilayered construct of claim 9.

11. The implantable prosthesis of claim 10, wherein the implantable prosthesis is a prosthesis for the replacement or patching of blood vessels, skin, cartilage, tendons, ligaments, cardiac tissue, stomach, esophagus, intestines, uterine tubes, larynx, urethra or nerve guidance conduits.

12. The method of claim 1, further comprising repeating steps (a) and (b) to obtain a desired number of layers before performing step (c).

13. The method of claim 1, further comprising repeating step (c) to obtain a desired number of layers.

14. The method of claim 1, further comprising repeating steps (a) to (c) to obtain a desired number of layers.

15. The method of claim 1, further comprising preconditioning a resultant multilayered composite sheet by stretching and relaxing it.

16. The method according to claim 15, wherein the composite is stretched to at least 120% of its original length.

17. The method according to claim 15, wherein the composite is stretched to at least 130% of its original length.

18. The method according to claim 15, wherein the composite is stretched and relaxed at least 2 times.

19. The method according to claim 15, wherein the composite is stretched and relaxed at least 5 times.

20. The method of claim 1, wherein the multilayered construct is a multilayered hollow tube.

21. The method of claim 1, wherein the polymer fiber is selected from polymer fibers comprising degradable poly(ester carbonate urethane)urea (PECUU), poly(carbonate urethane)urea (PCUU) and polycaprolactone.

22. The method of claim 1, wherein the polymer fiber comprises polycaprolactone.

23. The method of claim 1, wherein the multilayered construct is a multilayered hollow tube and the polymer fiber comprises polycaprolactone.

\* \* \* \* \*